United States Patent
Levy

(10) Patent No.: US 6,395,029 B1
(45) Date of Patent: May 28, 2002

(54) SUSTAINED DELIVERY OF POLYIONIC BIOACTIVE AGENTS

(75) Inventor: Robert J. Levy, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/234,011

(22) Filed: Jan. 19, 1999

(51) Int. Cl.[7] .................. A61F 2/00; C07H 19/00; A61K 9/00; A61L 27/40
(52) U.S. Cl. .................. 623/11.11; 623/23.59; 623/1.42; 427/2.24; 427/2.31; 424/450; 424/484; 424/490
(58) Field of Search .................. 623/11.11, 23.59, 623/1.42; 427/2.24, 2.31; 424/450, 484, 490

(56) References Cited

U.S. PATENT DOCUMENTS

| | | | |
|---|---|---|---|
| 4,160,452 A | | 7/1979 | Theeuwes |
| 4,256,108 A | | 3/1981 | Theeuwes |
| 4,265,874 A | | 5/1981 | Bonsen et al. |
| 4,828,563 A | * | 5/1989 | Mueller-Lierheim ......... 623/16 |
| 5,034,506 A | | 7/1991 | Summerton et al. |
| 5,354,844 A | * | 10/1994 | Beug et al. .................. 530/345 |
| 5,660,854 A | * | 8/1997 | Haynes et al. ............... 424/450 |
| 5,700,286 A | * | 12/1997 | Tartaglia et al. ............... 623/1 |
| 5,753,261 A | * | 5/1998 | Fernandez et al. .......... 424/450 |
| 5,756,476 A | * | 5/1998 | Epstein et al. ................. 514/44 |

OTHER PUBLICATIONS

Bello et al., 1985, J. Biomol. Struct. Dyn. 2:899–913.
Brem et al., 1995, J Neurooncol. 26:111–123.
Chen et al., 1994, Hum. Gene Ther. S:429–435.
Cox, D.A., 1995, Cell Biology International 19: 357–371.
Duguid et al., 1998, Biophys. J. 74:2802–2814.
Fasbender et al., 1996, J. Biol. Chem. 272:6479–6489.
Fung et al., 1988, Cancer Res. 58:672–684.
Jones et al., 1997, Vaccine 15:814–817.
Lasic, 1997, In: *Gene Delivery*, Lipsows, Ed., CRC Press, Boca Raton, Florida, pp. 33–37 and 56–61.
Lavitrano et al., 1992, Mol. Reprod. Dev. 31:161–169.
Martinez–Fong et al., 1994, Hepatology 20: 1602–1608.
Maruyama et al., 1997, Bioconj. Chem. 8:735–742.
Mathiowitz et al., 1997, Nature 386:410–414.
Nielsen et al., 1991, Science 254: 1497.
Niidome et al., 1997, J. Biol. Chem. 272:15307–15312.
Nygren et al., 1998, Biopolymers 46:39–51.
Orkin et al., 1995, "Report and Recommendations of the Panel to Assess the NIH Investment in Research on Gene Therapy", National Institutes of Health, Bethesda, MD.
Schneider et al., 1990, Tetrahedron Lett. 31:335.
Slavin, 1995, Cell Biol. Intl. 19:431–444.
Song et al., 1997, J. Controlled Release 43:197–212.
Sorgi et al., 1997, Gene Therapy 4:961–968.
Sosnowski et al., 1996, J. Biol. Chem. 271:33647–33653.
Uhlmann et al., 1990, Chem. Rev. 90:543–584.
Wadhwa et al, 1995, Bioconj. Chem. 6:283–291.
Wolfert et al., 1996, Human Gene Therapy 7:2123–33.
Wolfert et al., 1996, Gene Therapy 3:269–273.

* cited by examiner

*Primary Examiner*—Corrine McDermott
*Assistant Examiner*—Choon P. Koh
(74) *Attorney, Agent, or Firm*—Foley & Lardner

(57) ABSTRACT

The invention relates to compositions and methods for delivering a polyionic bioactive composition such as a nucleic acid to a tissue of an animal. The compositions of the invention include compositions which comprise a matrix comprising the polyionic bioactive agent and wherein at least most of the polyionic bioactive agent at the exterior portion of the matrix is present in a condensed form. The invention also includes methods of making such compositions, including particles, devices, bulk materials, and other objects which comprise, consist of, or are coated with such compositions. Methods of delivering a polyionic bioactive agent to an animal tissue are also described. The invention further includes a method of storing a nucleic acid.

44 Claims, 2 Drawing Sheets

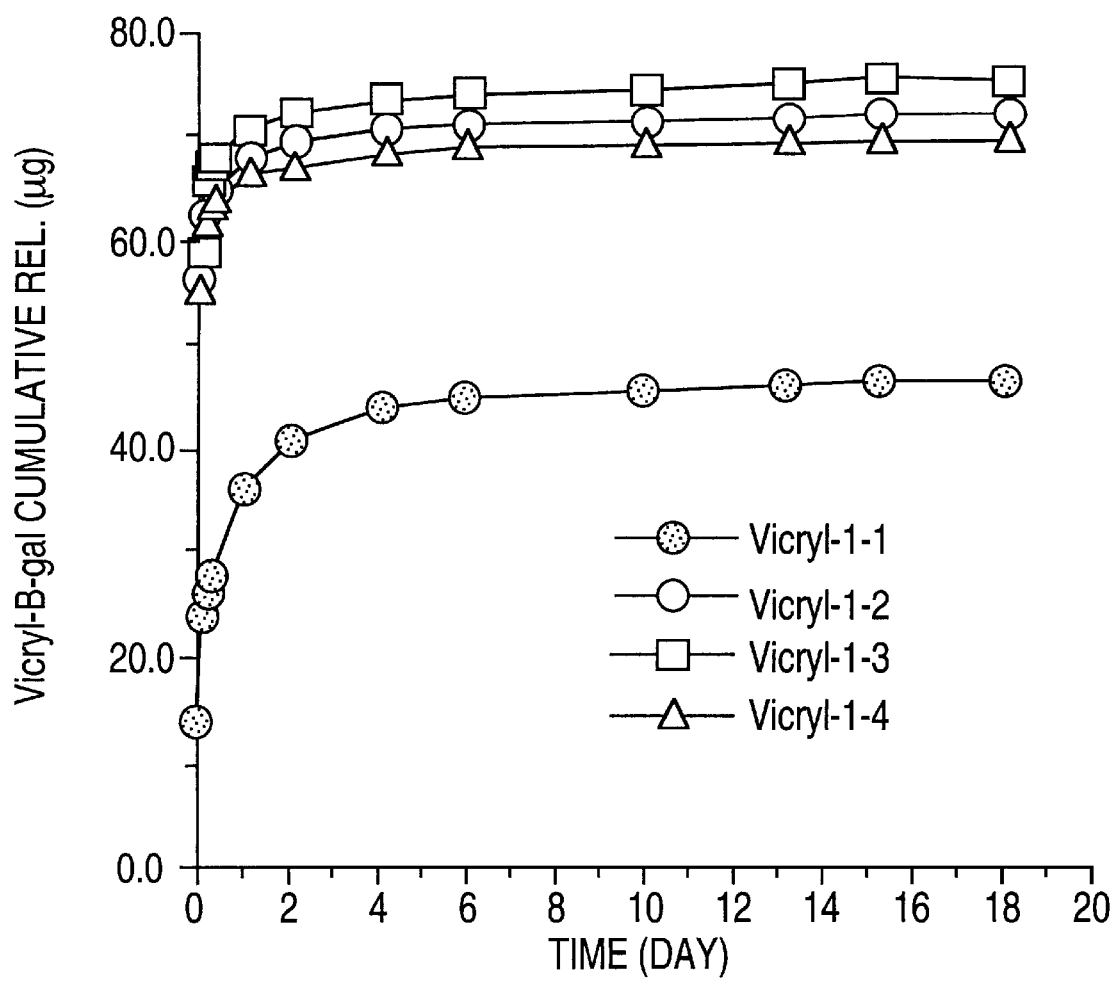

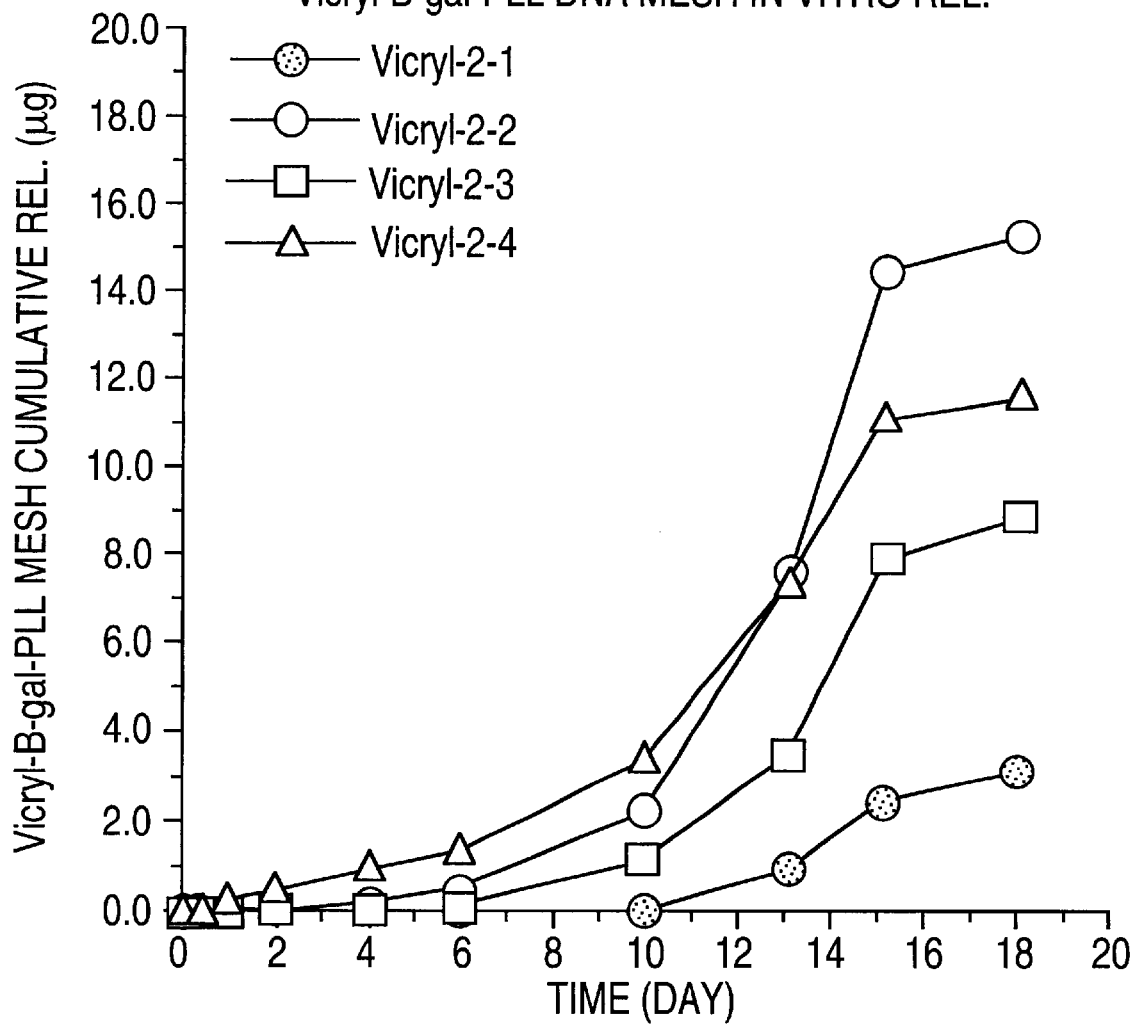

SUSTAINED DELIVERY OF POLYIONIC BIOACTIVE AGENTS

FIELD OF THE INVENTION

The field of the invention is drug delivery, including nucleic acid delivery.

BACKGROUND OF THE INVENTION

Delivery of one or more types of biologically active molecule to an animal or to an animal tissue forms the basis of modern pharmacology. In order to achieve the fullest therapeutic or prophylactic effect, the composition and method used to deliver the bioactive agent must provide the proper amount of the agent to the appropriate tissue(s) of the animal, in an active or activatable form, at an appropriate point in time, and for a sufficient duration. Despite thousands of years of pharmacological research and practice, there remains a critical need for compositions and methods of delivering polyionic bioactive agents, particularly in a sustained-release manner.

Numerous polyionic bioactive agents are known in the art, including both polyanionic and polycationic bioactive agents. Nucleic acids, in particular, have proven difficult to deliver effectively to the animal and in a sustained-release manner. The difficulties in delivering nucleic acids have persisted despite the intense and increasing desire of researchers and clinicians to be able to deliver nucleic acids to animal tissues, particularly to human tissues. In December, 1995, the U.S. National Institutes of Health issued a "Report and Recommendations of the Panel to Assess the NIH Investment in Research on Gene Therapy (Orkin et al., 1995, National Institutes of Health, Bethesda, Md.). In this Report, it was recognized that the development of gene therapy approaches to disease treatment was being inhibited, in part, by a dearth of effective gene transfer vectors. The Report recognized a need for further research applied to improving vectors for gene delivery.

Among the physiological phenomena which can inhibit administration of a nucleic acid to an animal tissue are the following.

Inability to direct the nucleic acid to cells of the desired tissue.

Inability of the nucleic acid to cross membranes of cells of the desired tissue.

Nucleolytic digestion of the nucleic acid prior to its delivery to cells of the desired tissue.

Nucleolytic digestion of the nucleic acid within cells of the desired tissue prior to transfer of the nucleic acid to a location within the cells at which the nucleic acid may exert its intended effect.

Clearance of the nucleic acid from the animal's system before the nucleic acid has been delivered to a sufficient fraction of cells of the desired tissue.

Inability to achieve an adequate dosage of the nucleic acid at the desired tissue.

A desirable nucleic acid vector will permit administration that is not significantly inhibited by these phenomena.

Numerous compositions and methods are known for delivering a nucleic acid to an animal tissue. Such compositions include "naked" (i.e. non-complexed) nucleic acids, nucleic acids complexed with cationic molecules such as polylysine and liposome-forming lipids, and virus vectors.

Naked nucleic acids can be taken up by various animal cells, but are subject to nucleolysis, both inside and outside of cells that take them up. For example, it is known that cells in wounded tissue (e.g. cells lining an incision made in a tissue) are particularly amenable to taking up naked nucleic acids. Examples of such cells include, but are not limited to, fibroblasts, capillary endothelial cells, capillary pericytes, mononuclear inflammatory cells, segmented inflammatory cells, and granulation tissue cells.

The use of nucleic acid analogs which are relatively resistant to nucleolysis is known. Such analogs include, for example, phosphorothioate nucleic acid analogs. However, in some situations, particularly where incorporation of the nucleic acid into the genome of the target cell is desired, the use of nucleic acid analogs can be undesirable. Targeting of naked nucleic acid vectors to particular animal tissues can be difficult, particularly in situations in which the tissue is normally bathed by a liquid in which the vector may be carried away from the tissue site.

Compositions for sustained release of naked nucleic acids are known, but such compositions have many of the same drawbacks of other naked nucleic acid vectors, namely, that the nucleic acids released from the compositions may not be efficiently taken up by cells of the desired tissue and that the nucleic acids released from the compositions are susceptible to nucleolysis. Examples of such compositions include compositions comprising naked nucleic acids in a biodegradable polymer matrix. Another shortcoming of such compositions is that they can be difficult to target to specific tissues in order to achieve localized delivery of the nucleic acid. Such compositions generally occur in liquid form, which must be injected at the desired site, but is capable of flowing from the site of administration to other sites.

Numerous vectors comprising a nucleic acid complexed with a compound to improve stability or uptake of the nucleic acid by a target cell have been described. Such compounds include, by way of example, calcium phosphate, polycations such as diethylaminoethyl-dextran, polylysine, or polybrene, and liposome-forming lipids such as didocyl-methylammonium bromide and Lipofectamine™. Many of these compounds are toxic, or produce undesired reactions, when administered to patients. Thus, while nucleic acid vectors comprising a nucleic acid complexed with one of these compounds may be useful for transfection of cultured cells, these vectors are not useful for delivering nucleic acids to cells in an animal tissue.

Virus vectors are generally regarded as the most efficient nucleic acid vectors. Recombinant replication-defective virus vectors have been used to transduce (i.e., infect) animal cells both in vitro and in vivo. Such vectors have included retrovirus, adenovirus, adeno-associated virus vectors, and herpes virus vectors. While highly efficient for gene transfer, a major disadvantage associated with the use of virus vectors is the inability of many virus vectors to infect non-dividing cells. Another serious problem associated with the use of virus gene vectors is the potential for such vectors to induce an immune response in a patient to whom they are administered. Such an immune response limits the effectiveness of the virus vector, since the patient's immune system rapidly clears the vector upon repeated or sustained administration of the vector. Furthermore, insertion of a gene into the genome of a cell by a virus vector may induce undesirable mutations in the cell. Other problems associated with virus gene vectors include inability to appropriately regulate gene expression over time in transfected cells, potential production and transmission to other humans of harmful virus particles, local and general toxicity, undesirable immunogenicity, and unintended disruption of target or other cell metabolism.

What is needed are compositions and methods which can be used to deliver nucleic acids to cells of a desired tissue in an animal in a form in which the nucleic acid can cross the cell membranes in a relatively nuclease-resistant form, preferably for a period sufficient to permit the nucleic acid to enter a substantial fraction of the cells of the desired tissue. Also preferably, the nucleic acid vector should not induce toxicity or other significantly harmful reactions in the animal.

Proteins are another class of polyionic bioactive agents which have proven to be difficult to administer to animal tissues in many cases. Proteins, often being very large molecules, are difficult to transfer across a cell membrane. In addition, certain proteins, including integral membrane proteins such as certain membrane-bound receptors, must be inserted into the cell membrane in the correct orientation in order to exhibit their characteristic biological activity. Furthermore, proteins are susceptible to degradation by the action of proteolytic enzymes, which are common in biological systems. Proteins may be delivered to a tissue as the intact protein, as subunits which assemble at the site of delivery, as propeptides which are proteolytically cleaved at the site of delivery to yield active protein or protein subunits, or in the form of one or more nucleic acids which encode the protein or its constituent subunits. Delivery of nucleic acids encoding the protein or its subunits has the advantages that the nucleic acids may be easier to transfer across the cell membrane, that they are not subject to proteolysis, and that expression of the protein from the nucleic acids may result in properly oriented, active protein. A significant need exists for compositions and methods of delivering a protein to a tissue of an animal.

The compositions and methods of the present invention satisfy the needs identified above.

BRIEF SUMMARY OF THE INVENTION

The invention relates to a composition for delivery of a polyionic bioactive agent. The composition comprising the polyionic bioactive agent and a matrix having an exterior portion. At least most of the polyionic bioactive agent present at the exterior portion of the matrix is in a condensed form. In one embodiment, substantially all of the polyionic bioactive agent present at the exterior portion of the matrix is in a condensed form. In another embodiment, the exterior portion has an exterior surface, and the polyionic bioactive agent is present substantially only on the exterior surface of the exterior portion of the matrix. The matrix may, of course, comprise a plurality of the exterior portions.

In one aspect of the composition of the invention, the matrix further comprises an interior portion having the polyionic bioactive agent suspended therein, and less than most of the polyionic bioactive agent suspended in the interior portion of the matrix is not in a condensed form. In this aspect, the matrix may comprise a plurality of alternating the exterior portions and the interior portions.

In another aspect of the composition of the invention, the exterior portion comprises a polyionic condensing agent having a charge opposite that of the polyionic bioactive agent. Preferably, the polyionic bioactive agent is a polyanionic bioactive agent, and the polyionic condensing agent is a polycationic condensing agent, such as one selected from the group consisting of a polylysine, polyarginine, polyornithine, polyhistidine, myelin basic protein, a low molecular weight glycopeptide, a cationic amphiphilic alpha-helical oligopeptide having a repeating sequence, a galactosylated histone, $Mg^{2+}$, $Ca^{2+}$, $Co^{3+}$, $La^{3+}$, $Al^{3+}$, $Ba^{2+}$, $Cs^+$, polybrene, spermine, spermidine, prolamine, polyethylenimine, putrescine, cadaverine, and hexamine. Preferably, the polycationic condensing agent is poly-L-lysine.

Exemplary polyanionic bioactive agents include, but are not limited to, a nucleic acid, a nucleic acid analog, a plasmid, a linear DNA molecule, a linear RNA molecule, an antisense oligonucleotide, an expression vector, a transformation vector, a transfection vector, a ribozyme, a transcribable vector comprising a DNA molecule encoding a ribozyme, a viral fragment, a cosmid, a DNA molecule encoding a portion of the genome of an organism, a cDNA molecule, a gene fragment, a single-stranded DNA molecule, a double stranded DNA molecule, a supercoiled DNA molecule, a triple-helical DNA molecule, and a Z-DNA molecule.

In certain embodiments, the polyanionic bioactive agent is selected from the group consisting of an expression vector encoding a wound healing therapeutic protein, an expression vector encoding an anti-restenotic protein, and an anti-restenotic antisense oligonucleotide. The wound healing therapeutic protein may, for example, be selected from the group consisting of TGF-β, FGF, PDGF, IGF, M-CGF, BMP, GH, and PTH. The anti-restenotic protein may, for example, be selected from the group consisting of TPA, TGF-β, FGF, Rb, p21, and TK. The anti-restenotic antisense oligonucleotide may, for example, be selected from the group consisting of a c-myb antisense oligonucleotide, a c-myc antisense oligonucleotide, and a PCNA antisense oligonucleotide.

In one embodiment of the composition of the invention, the polyionic bioactive agent is a polycationic bioactive agent, and the polyionic condensing agent is a polyanionic condensing agent. The polyanionic condensing agent may, for example, be a nucleic acid. The polycationic bioactive agent may, for example, be selected from the group consisting of a DNA-binding protein, a histone, a cationic protein, a polyamine, cadaverine, putrescine, spermidine, and spermine.

In another embodiment of the composition of the invention, the matrix is selected from the group consisting of a charged biocompatible material, a biocompatible polymer, a biodegradable polymer, a biocompatible biodegradable polymer, polylactic acid, polyglycolic acid, polycaprolactone, a copolymer of polylactic acid and polyglycolic acid, a copolymer of polylactic acid and polycaprolactone, a copolymer of polyglycolic acid and polycaprolactone, a polygylcolide, a polyanhydride, a polyacrylate, a polyalkyl cyanoacrylate, n-butyl cyanoacrylate, isopropyl cyanoacrylate, a polyacrylamide, a polyorthoester, a polyphosphazene, a polypeptide, a polyurethane, a polystyrene, a polystyrene sulfonic acid, a polystyrene carboxylic acid, a polyalkylene oxide, a polyethylene, a polyvinyl chloride, a polyamide, a nylon, a polyester, a rayon, a polypropylene, a polyacrylonitrile, an acrylic, a polyisoprene, a polybutadiene, a polybutadiene-polyisoprene copolymer, a neoprene, a nitrile rubber, a polyisobutylene, an olefinic rubber, an ethylene-propylene rubber, an ethylene-propylene-diene monomer rubber, a polyurethane elastomer, a silicone rubber, a fluoroelastomer, a fluorosilicone rubber, a vinyl acetate homopolymer, a vinyl acetate copolymer, an ethylene vinyl acetate copolymer, an acrylates homopolymer, an acrylates copolymer, polymethylmethacrylate, polyethylmethacrylate, polymethacrylate, ethylene glycol dimethacrylate, ethylene dimethacrylate, hydroxymethyl methacrylate, a polyvinylpyrrolidone, a polyacrylonitrile butadiene, a polycarbonate, a polyamide, a fluoropolymer, polytetrafluoroethylene, polyvinyl fluoride, a polystyrene, a styrene acrylonitrile homopolymers, a styrene acrylonitrile copolymer, a cellulose acetate, an acrylonitrile butadiene styrene homopolymer, a acrylonitrile butadiene styrene copolymer, a polymethylpentene, a polysulfone, a polyester, a polyimide, a polyisobutylene, a polymethylstyrene, an alginate, an agarose, a dextrin, a dextran, a multiblock polymer, a biocompatible metal alloy, titanium, platinum, stainless steel, hydroxyapatite, tricalcium phosphate, cocoa butter, a wax, and a ceramic material. Preferably, the biodegradable polymer is a polylactate/polyglycolate copolymer.

The invention also relates to a surface coated with the composition of the invention.

The invention further relates to an implantable device having a surface coated with the composition of the invention. The device may, for example, be selected from the group consisting of a wound dressing, a suture, a particle, a vascular stent, and a bulk material.

When the device is a vascular stent, the biodegradable matrix is preferably a polylactate/polyglycolate copolymer, and the polyionic bioactive agent is preferably a nucleic acid selected from the group consisting of an expression vector encoding an anti-restenotic protein and an anti-restenotic antisense oligonucleotide, and wherein the exterior portion further comprises polylysine. The anti-restenotic protein may, for example, be selected from the group consisting of TPA, TGF-β, FGF, Rb, p21, and TK. The anti-restenotic antisense oligonucleotide may, for example, be selected from the group consisting of a c-myb antisense oligonucleotide, a c-myc antisense oligonucleotide, and a PCNA antisense oligonucleotide.

When the device is a suture coated with a plurality of layers of the matrix, the biodegradable matrix is preferably a polylactate/polyglycolate copolymer, and the polyionic bioactive agent is preferably a nucleic acid expression vector encoding a wound healing therapeutic protein. The wound healing therapeutic protein may, for example, be selected from the group consisting of TGF-β, FGF, PDGF, IGF, M-CGF, BMP, GH, and PTH. Preferably, suture is coated with at least twenty layers of the matrix.

When the device is a particle, the polyanionic bioactive agent is preferably selected from the group consisting of an expression vector encoding a wound healing therapeutic protein, an expression vector encoding an anti-restenotic protein, and an anti-restenotic antisense oligonucleotide. The wound healing therapeutic protein may, for example, be selected from the group consisting of TGF-β, FGF, PDGF, IGF, M-CGF, BMP, GH, and PTH. The anti-restenotic protein may, for example, be selected from the group consisting of TPA, TGF-β, FGF, Rb, p21, and TK. The anti-restenotic antisense oligonucleotide is selected from the group consisting of a c-myb antisense oligonucleotide, a c-myc antisense oligonucleotide, and a PCNA antisense oligonucleotide. Preferably, the particle has a diameter no greater than about 900 micrometers, and more preferably no greater than about 1 micrometer.

When the device is a bulk material, the polyanionic bioactive agent is preferably selected from the group consisting of an expression vector encoding an oncogene and an antisense oligonucleotide directed against an oncogene. The oncogene may, for example, be selected from the group consisting of abl, akt2, apc, bcl2α, bcl2β, bcl3, bcr, brcal, brca2, cbl, ccnd1, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf1, wnt1, wnt2, wt1, and yes1.

When a surface is coated with the composition of the invention having an interior portion having the polyionic bioactive agent suspended therein, the interior portion is preferably interposed between the surface and the exterior portion of the matrix. Thus, for example, when an implantable device has a surface coated with the composition having such an interior portion, the interior portion is preferably interposed between the surface of the device and the exterior portion of the matrix.

The invention also relates to a method of making a composition for delivery of a polyionic bioactive agent. This method comprises providing a biodegradable matrix having an interior portion and an exterior portion and contacting the exterior portion of the biodegradable matrix with a polyionic condensing agent having a charge opposite that of the polyionic bioactive agent. The polyionic bioactive agent is suspended in the biodegradable matrix in a non-condensed form. At least most of the polyionic bioactive agent assumes a condensed form at the exterior portion of the biodegradable matrix when it is contacted with the polyionic condensing agent.

The invention further relates to a method of making a composition for delivery of a polyionic bioactive agent. This method comprises providing a matrix which has an exterior portion and which comprises the polyionic bioactive agent at the exterior portion; and contacting the exterior portion of the matrix with a polyionic condensing agent having a charge opposite that of the polyionic bioactive agent. At least most the polyionic bioactive agent assumes a condensed form at the exterior portion of the matrix.

The invention still further relates to a method of delivering a polyionic bioactive agent to an animal tissue. This method comprising placing in fluid communication with the animal tissue a composition comprising the polyionic bioactive agent and a matrix having an exterior portion. At least most of the polyionic bioactive agent is in a condensed form at the exterior portion of the matrix.

The invention also relates to a kit comprising a biocompatible matrix having an exterior portion and an instructional material which describes combining the matrix with a polyionic bioactive agent and condensing at least most of the polyionic bioactive agent at the exterior portion of the matrix.

The invention relates to another kit, this kit comprising a composition which comprises the polyionic bioactive agent and a biocompatible matrix having an exterior portion. At least most of the polyionic bioactive agent present at the exterior portion of the matrix is in a condensed form. The kit further comprises an instructional material which describes administration of the composition to a tissue of an animal to effect delivery of the polyionic bioactive agent to the tissue.

In another aspect, the invention relates to a kit for coating an implantable device with a composition for delivery of a polyionic bioactive agent upon implantation of the device. This kit comprises a biocompatible polymeric matrix suspended in a solvent and a polyionic condensing agent having a charge opposite that of the polyionic bioactive agent.

The invention also includes a kit for coating an implantable device with a composition for delivery of a polyionic bioactive agent upon implantation of the device. This kit comprising a suspension of monomers of a biocompatible polymeric matrix, a polymerization initiator, and a polyionic condensing agent having a charge opposite that of the polyionic bioactive agent.

The invention further includes a method of storing a nucleic acid. This storage method comprises suspending the nucleic acid in a matrix and contacting the matrix with a polycationic condensing agent.

BRIEF DESCRIPTION OF THE DRAWINGS

FIG. 1, comprising FIGS. 1A and 1B, is a pair of graphs which depict release of DNA over time from PLGA/DNA-coated polyester meshes upon incubation of the meshes with a solution having a pH of 7.4 at 37° C. The meshes which yielded the results depicted in FIG. 1A were not treated with polylysine. The meshes which yielded the results depicted in FIG. 1B were treated with a polylysine-containing solution for one hour and dried prior to incubation.

DETAILED DESCRIPTION

The invention is based on the discovery that sustained-release delivery of a polyionic bioactive agent may be improved by providing a composition comprising a matrix and the agent in a condensed form. The compositions and methods of the invention are particularly useful for delivery of a nucleic acid to a tissue of an animal. However, the compositions and methods of the invention are not limited to this use. For example, the compositions of the invention are also useful for long-term, stable storage of nucleic acids.

The compositions of the invention comprise a polyionic bioactive agent and a matrix. The matrix has an exterior portion, and the polyionic bioactive agent present at the exterior portion of the matrix is in a condensed form. In one embodiment, the exterior portion of the matrix comprises a polyionic condensing agent having a charge opposite that of the polyionic bioactive agent. Combination of the polyionic bioactive agent with the oppositely-charged polyionic condensing agent causes the polyionic bioactive agent to assume a condensed form. In this condensed form, the bioactive agent is more stable and, in many instances, better able to traverse a cell membrane than it is in its non-condensed form.

The compositions of the invention may comprise particles or other solid forms which are completely biodegradable (i.e. which, following degradation of the biodegradable matrix and delivery or dispersal of the bioactive agent and the condensing agent, yield no, or substantially no, residue). Alternately, the compositions of the invention may be used to coat all or part of a surface of a solid object. The solid object may be biodegradable, or it may be non-biodegradable. Non-limiting examples of solid objects which may be wholly or partially coated with the compositions of the invention include biodegradable polymer particles, non-biodegradable ceramic particles, surgical sutures, and vascular stents.

The compositions of the invention comprise a matrix having an exterior portion which comprises a polyionic bioactive agent in a condensed form. The bioactive agent may be present substantially only on the exterior surface of the matrix. For example, the composition may be a stainless steel matrix formed in the shape of a vascular stent and having condensed DNA adhered to one or more surfaces of the stent. Alternately, the exterior portion of the matrix may have the bioactive agent suspended in therein in a condensed form. By way of example, the composition may be a porous polymeric matrix comprising the bioactive agent adhered to the surface thereof, suspended therein, or both. By contacting the composition with a solution comprising the condensing agent, the solution is enabled to contact the bioactive agent, whereby the bioactive agent is condensed. Thus, the exterior portion of the matrix of the compositions of the invention may have condensed polyionic bioactive agent adhered to the surface thereof, within the bulk of the matrix of the exterior portion, or both.

In one embodiment of the compositions of the invention, the matrix comprises an interior portion of the matrix that comprises the polyionic bioactive agent in a non-condensed form. There may be a sharp delineation between the interior portion of the matrix and the exterior portion of the matrix or there may be a gradual decrease in the proportion of the bioactive agent which is present in a condensed form with, for example, at least most of the bioactive agent in the exterior portion of the matrix in a condensed form, with substantially none of the bioactive agent in the interior portion of the matrix in a condensed form. Preferably, less than most of the bioactive agent suspended in the interior portion of the matrix is in a condensed form, although very little (e.g. 10 mole % or 20 mole %) or even substantially none (i.e.<1 mole %) or none of the bioactive agent in the interior portion may be in a condensed form.

The composition may have a plurality of exterior portions, a plurality of interior portions, or both. By way of example, the composition may comprise an object having a plurality of surfaces coated with the matrix, the matrix having an exterior portion on each of the surfaces. Alternately, the matrix may comprise multiple portions, in some or all of which at least most of the bioactive agent is present in a condensed form. Further by way of example, the composition may comprise an object coated with a layer of matrix comprising the polyionic bioactive agent, the layer of matrix comprising an interior portion interposed between a surface of the object and the exterior portion of the matrix. The object may have one or more additional layers of matrix, wherein for each additional layer of matrix, an interior portion of the additional layer of matrix is interposed between the exterior portion of the previous layer of matrix and the exterior portion of the additional layer of matrix. Depending on the proportion of the bioactive agent that is present in a condensed form at the innermost portion of the additional layer, the additional layers may comprise only exterior portions (i.e. wherein at least most of the bioactive agent is present in a condensed form), or they may comprise both exterior portions and interior portions (i.e. wherein less than most of the bioactive agent in the interior portion is present in a condensed form). For any layer of matrix in these multi-layer compositions, each layer may comprise only an exterior portion, only an interior portion, or both an exterior portion and an interior portion. The number or layers may be as few as one, and may be five, ten, fifty, one hundred, several hundred, or more. At least one layer must comprise an exterior portion, as defined herein, and the outermost layer preferably comprises an exterior portion.

The compositions of the invention are particularly amenable to use on implantable devices. The devices may be fashioned from or partially or entirely coated with a composition of the invention. Non-limiting examples of devices which comprise the composition of the invention include particles consisting of the composition, particles having one or more surfaces coated with the composition, particles of the composition having one or more surfaces coated with another material, a bulk solid consisting of the composition, a bulk solid comprising the composition, a bulk solid having one or more surfaces coated with the composition, a mechanical device comprising the composition, a mechanical device fashioned from the composition, a mechanical device having one or more surfaces coated with the composition, a surgical suture comprising the composition, a surgical suture fashioned from the composition, a surgical suture coated with the composition, a vascular stent comprising the composition, a vascular stent fashioned from the composition, and a vascular stent having one or more surfaces coated with the composition.

Exemplary materials which may be used in the compositions of the invention are now described. It is understood, however, that the materials described herein represent only non-limiting examples of materials which may be used. In light of the present disclosure, it will be evident to the skilled artisan how materials which are not specifically listed here, or which are hereafter developed or discovered, may be used to make the composition of the invention.

The Polyionic Bioactive Agent of the Composition of the Invention

The polyionic bioactive agent may be any bioactive agent having at least two, at least five, at least ten, or, preferably, at least twenty ionically charged groups at the physiological pH of human blood (i.e. about pH 7.4). The polyionic bioactive agent may be a polyanion, a polycation, or a bioactive agent having at least one negative charge and at least one positive charge at the physiological pH of human blood. Alternatively, the charge on the polyionic bioactive agent may be expressed in terms of $\zeta$-potential. When the polyionic bioactive agent is a polyanionic bioactive agent, it preferably has a $\zeta$-potential of at least about −5 millivolts to about −10 mV, more preferably at least about −20 mV to about −25 mV. Examples of polycationic bioactive agents which may be used in the compositions and methods of the invention include DNA-biding proteins such as histones, other cationic proteins such as protamines and various transcription factors (e.g. NFATε1), polyamines such as cadaverine, putrescine, spermidine, and spermine. Preferably, however, the polyionic bioactive molecule is a polyanionic bioactive agent such as a nucleic acid.

The identity of the polyanionic bioactive agent is not critical. A wide variety of polyanionic bioactive agents may be used. Preferably, the polyanionic bioactive agent invention is a nucleic acid. The nucleic acid may be a naturally-occurring nucleic acid, a recombinant nucleic acid, or another type of synthetic nucleic acid. By way of example, the nucleic acid may be replicated or amplified using as a template a naturally-occurring nucleic acid obtained from a viral, bacterial, animal, or plant source. The nucleic acid may, for example, be DNA or RNA and may exist in a double-stranded, single-stranded, or partially double-stranded form. Furthermore, the nucleic acid may be found as part of a virus or other macromolecule. (e.g. as in Fasbender et al., 1996, J. Biol. Chem. 272:6479–6489).

The nucleic acid useful in the present invention may be, by way of example and not limitation, an oligonucleotide or polynucleotide such as an antisense DNA molecule, an antisense RNA molecule, a catalytic RNA molecule or a catalytic RNA/protein complex (i.e. a "ribozyme"), an expression vector comprising a DNA molecule encoding a protein such as a therapeutic protein, a transcribable vector comprising a DNA molecule encoding a ribozyme, a viral fragment such as a viral DNA or RNA molecule, an RNA molecule encoding a protein such as a therapeutic protein, a plasmid, a cosmid, a DNA molecule encoding a portion of the genome of an organism, a cDNA molecule, a gene fragment; or a DNA molecule in any of its superstructural forms, including single-stranded DNA, double stranded DNA, supercoiled DNA, triple-helical DNA, Z-DNA, and the like.

Where the polyionic bioactive molecule is a nucleic acid, the nucleic acid may be prepared or isolated by any conventional means typically used to prepare or isolate nucleic acids. For example, DNA and RNA molecules may be chemically synthesized using commercially available reagents and synthesizers by methods that are well-known in the art (e.g., Gait, 1985, In: *Oligonucleotide Synthesis: A Practical Approach*, IRL Press, Oxford, England). RNA molecules may also be produced in high yield via in vitro transcription methods using plasmids such as SP65 (available from Promega Corporation, Madison, Wis.). The nucleic acids may be purified by any suitable means, as many such means are well known in the art. For example, the nucleic acids can be purified by reverse-phase or ion exchange HPLC, size exclusion chromatography, or gel electrophoresis. Of course, the skilled artisan will recognize that the method of purification will depend in part on the size and type of the nucleic acid to be purified.

Nucleic acids having modified internucleoside linkages may also be used in the compositions and methods of the invention. Nucleic acids containing modified internucleoside linkages may be synthesized using reagents and methods that are well known in the art. For example, methods for synthesizing nucleic acids containing phosphonate, phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2—$), dimethylene-sulfoxide ($—CH_2—SO—CH_2—$), dimethylene-sulfone ($—CH_2—SO_2—CH_2—$), 2'-O-alkyl, and 2'-deoxy-2'-fluoro-phosphorothioate internucleoside linkages are well known in the art (e.g. Uhlmann et al., 1990, Chem. Rev. 90:543–584; Schneider et al., 1990, Tetrahedron Lett. 31:335).

The nucleic acid may, for example, be a therapeutic agent, such as for example an antisense DNA molecule that inhibits mRNA translation. Alternately, by way of example, the nucleic acid may encode a therapeutic agent, such as a transcription or translation products which, when expressed by a cell to which the nucleic acid-containing composition is delivered, has a favorable therapeutic effect upon the cell. Exemplary therapeutic transcription products include antisense RNA molecules, ribozymes, viral fragments, and the like. Exemplary therapeutic translation products include proteins, such as, for example, membrane proteins, transcription factors, intracellular proteins, cytokine binding proteins, and the like.

In a preferred embodiment of the invention, the nucleic acid is a DNA molecule that encodes gene products that stimulate or promote healing of wounded or damaged tissues in vivo or alleviate the symptoms of disease. Particularly preferred are therapeutic proteins, such as growth factors and hormones. Particularly preferred growth factors are transforming growth factor-beta (TGF-$\beta$; Cox, D. A., 1995, *Cell Biology International* 19: 357–371), acidic fibroblast growth factor (FGF; Slavin, 1995, Cell Biol. Intl. 19:431–444), platelet derived growth factor (PDGF), insulin like growth factor (IGF), macrophage-colony stimulating factor (M-CSF), and bone morphogenic protein(s) (BMPs); particularly preferred hormones are human growth hormone (GH) and human parathyroid hormone (PTH).

In another preferred embodiment of the invention, the nucleic acid is selected from an expression vector encoding an anti-restenotic protein and an anti-restenotic antisense oligonucleotide. Exemplary anti-restenotic proteins include, but are not limited to, tissue plasminogen activator (TPA), TGF-$\beta$, FGF, retinoblastoma protein (Rb), p21, and thymidine kinase (TK, i.e. with associated ganciclovir therapy). Exemplary anti-restenotic antisense oligonucleotides include, but are not limited to, a c-myb antisense oligonucleotide, a c-myc antisense oligonucleotide, and a PCNA antisense oligonucleotide.

Modified gene sequences, i.e. genes having sequences that differ from the gene sequences encoding the native proteins, are also encompassed by the invention, so long as the modified gene encodes and expresses a protein that exhibits the biological activity of the native protein, at a greater or lesser level of activity. These modified gene sequences include modifications caused by point mutations, modifications due to the degeneracies of the genetic code or naturally occurring allelic variants, and further modifications that are introduced by genetic engineering, i.e., by the hand of man, to produce recombinant nucleic acid molecules.

The nucleic acid useful in the compositions and methods of the invention may be recombinantly engineered into a variety of well known host vector systems that provide for replication of the nucleic acid on a large scale for the preparation of the composition of the invention. These vectors can be designed, using well known methods, to contain the elements necessary for directing transcription, translation, or both, of the nucleic acid. Methods which are well known to the skilled artisan can be used to construct expression vectors having the protein coding sequence operably linked with appropriate transcriptional/translational control signals. These methods include in vitro recombinant DNA techniques and synthetic techniques (see, e.g. Sambrook et al., 1989, *Molecular Cloning: A Laboratory Manual*, Cold Spring Harbor Laboratory, New York; Ausubel et al., 1997, *Current Protocols in Molecular Biology*, John Wiley & Sons, New York).

The genes encoding the proteins of interest may be operatively associated with a variety of different promoter/regulator sequences. The promoter/regulator sequences may be selected to optimize expression of therapeutic amounts of protein. In some instances, the promoter/regulator sequences may be constitutive or inducible promoters and can be used under the appropriate conditions to direct high level or regulated expression of the gene of interest.

It is also within the scope of the invention that the nucleic acid of the compositions and methods of the invention contains a plurality of protein-coding regions, combined on a single genetic construct under control of one or more promoters, or prepared as separate constructs of the same or different types, may be used. Alternately, the two or more protein-coding regions may be under the transcriptional control of a single promoter, and the transcript of the nucleic acid may comprise one or more internal ribosome entry sites interposed between the protein-coding regions. Thus, an almost endless combination of different genes and genetic constructs may be employed. Any and all such combinations are within the scope of the present invention.

Polyanionic bioactive agents other than nucleic acids are also useful in the compositions and methods of the present invention. Examples of such polyanionic bioactive agents include many proteins, such as β-lactoglobulin, phycocyanin, bone acidic glycoprotein (BAG75; which has a mass of about 75,000 Daltons), and other phosphoproteins of bones and teeth, and glycosaminoglycans such as heparin, heparan sulfate, chondroitin sulfate, polyuronic acid, and hyaluronic acid.

The Matrix of the Composition of the Invention

The matrix of the composition of the invention may be substantially any material into or onto which the polyionic bioactive agent of the invention may be incorporated. Preferably, the matrix is biocompatible. Also preferably, the matrix comprises a polymeric material.

A great many polymer materials are suitable for making the composition of the invention. Depending on the manner in which delivery of the polyionic bioactive agent is contemplated, the polymeric matrix may be non-biodegradable, or, preferably, biodegradable. The polymers may be a naturally-occurring polymer or a synthetic polymer. Discussion and a non-limiting list of suitable polymers can be found in Mathiowitz et al., P.C.T. publication number WO95/24929 (particularly at pages 6–9), and Goldstein et al., P.C.T. publication number WO97/47254 (particularly pages 22–35). Particularly preferred polymers for use in the compositions of the present invention include biocompatible biodegradable polymers such as polylactic acid, polyglycolic acid, polycaprolactone, and copolymers thereof. In preferred embodiments, the biocompatible biodegradable polymer is a copolymer of polylactic acid and polyglycolic acid (PLGA copolymer). Also preferably, the proportion of lactate monomers to glycolate monomers in the PLGA copolymer ranges from near infinity (i.e. the polymer comprises essentially only lactate monomers) to a lactate:glycolate ratio of about 25:75. More preferably, the PLGA copolymer has a molecular weight in the range from about 5000 to 120,000. It is understood that the higher the proportion of lactate monomers to glycolate monomers is, the less rapidly the copolymer will be biodegraded. Similarly, a copolymer having a relatively low lactate:glycolate monomer ratio (i.e. 50:50 or 25:75) will release the polyanionic bioactive agent at a rate greater than the rate of a copolymer having a relatively high lactate:glycolate monomer ratio (i.e. 75:25 or 100:1). Other suitable biocompatible biodegradable polymers include, but are not limited to polyesters such as polyglycolides, polyanhydrides, polyacrylates, polyalkyl cyanoacrylates such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, polyanhydrides, biopolymers such as collagens and elastin, alginates, chitosans, glycosaminoglycans, and mixtures of such polymers.

The polymer used to form the matrix of the composition of the invention may also be non-biodegradable, so long as the polymer is biocompatible. Examples of biocompatible non-biodegradable polymers which are useful in the compositions of the invention include, but are not limited to, polyethylenes, polyvinyl chlorides, polyamides such as nylons, polyesters, rayons, polypropylenes, polyacrylonitriles, acrylics, polyisoprenes, polybutadienes and polybutadiene-polyisoprene copolymers, neoprenes and nitrile rubbers, polyisobutylenes, olefinic rubbers such as ethylene-propylene rubbers, ethylene-propylene-diene monomer rubbers, and polyurethane elastomers, silicone rubbers, fluoroelastomers and fluorosilicone rubbers, homopolymers and copolymers of vinyl acetates such as ethylene vinyl acetate copolymer, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyvinylpyrrolidones, polyacrylonitrile butadienes, polycarbonates, polyamides, fluoropolymers such as polytetrafluoroethylene and polyvinyl fluoride, polystyrenes, homopolymers and copolymers of styrene acrylonitrile, cellulose acetates, homopolymers and copolymers of acrylonitrile butadiene styrene, polymethylpentenes, polysulfones, polyesters, polyimides, polyisobutylenes, polymethylstyrenes, and other similar compounds known to those skilled in the art.

Other biocompatible nondegradable polymers that are useful for making the matrix of the invention include those involving biocompatible metal ions or ionic coatings which can interact with DNA. Such metal ions include, but are not limited to gold and silver ions, $Al^{3+}$, $Fe^{3+}$, $Fe^{2+}$, $Mg^{2+}$, and $Mn^{2+}$. Gold and silver ions are particularly advantageous, for example, for inhibiting inflammation, binding DNA, and inhibiting infection and thrombosis.

The use of multiblock polymers in the matrix of the composition of the invention is contemplated. Such multiblock polymers may be biodegradable or not, and may be particularly useful to produce microspherical matrices, as described herein. Multiblock polymers comprise monomers of a plurality of types, wherein numerous monomers of a first type are polymerized and linked to a region comprising numerous polymerized monomers of a second type. Multiblock polymers may be used to facilitate production of microspheres, or to affect various properties of the microspheres. For example, subunits comprising an emulsifying agent may be incorporated into the multiblock polymer, obviating the need to add an emulsifying agent during production of microspheres using the polymer. Alternatively, hydrophobic or hydrophilic subunit blocks may be used to facilitate the incorporation of a wider variety of bioactive agents than are normally amenable to encapsulation in microspheres. Suitable multiblock copolymers, as well as their uses, are described in Levy et al., P.C.T. publication number WO96/20698, and Goldstein et al., P.C.T. publication number WO97/47254.

In a particularly preferred embodiment of the composition of the invention, the matrix of the composition is present in the form of microspheres or nanospheres. Preferably, the microspheres have a generally spherical shape and have a maximum physical dimension (analogous to the diameter of a sphere) of from about 1 micrometer to 900 micrometers, and more preferably from about 1 micrometer to 10 micrometers. Preferably, the nanospheres have a generally spherical shape and have a maximum physical dimension less than about 1 micrometer, more preferably less than about 300 nanometers, and even more preferably from about 70 nanometers to about 160 nanometers. Coatings for implantable or injectable particles or devices which comprise the composition comprising the matrix in a microspherical or nanospherical form are contemplated. Such particles and devices have the advantage of releasing microspheres or nanospheres over time, wherein the microspheres or nanospheres release the polyionic bioactive agent on a sustained basis.

Microspherical and nanospherical matrices are preferred because these forms are known to be amenable to penetration into mammalian tissues and uptake into mammalian cells. Furthermore, the total surface area of a composition comprising a matrix in the form of microspheres or nanospheres is greater than the total surface area of a bulk form of the same volume of matrix, meaning that biodegradation and/or release of the bioactive agent from the surface of the matrix may be increased if microspheres or nanospheres are used, rather than a bulk form of the matrix. Although the use of microspheres and nanospheres for delivery of pharmaceutical agents has been described by others, the use of such delivery vehicles to provide a polyionic bioactive agent in a condensed form to a mammalian tissue or cells has not been described by others.

The polymers used in producing the microspheres may optionally have other molecules bound to them. These modifications may, for example, impart the microspheres with the ability to target and bind specific tissues or cells, allow them be retained at the administration site, protect incorporated bioactive agents, exhibit antithrombogenic effects, prevent aggregation, and/or alter the release properties of the microspheres. Production of such modified polymers and surface-modified microspheres made from them are discussed in Levy et al., P.C.T. publication number WO96/20698, the disclosure of which is hereby incorporated by reference. The targeting agent may alternatively be bound to the polyionic condensing agent described herein. As a specific example, it may be desirable to incorporate receptor-specific molecules, such as antibodies, into or onto the microspheres to mediate receptor-specific particle uptake.

Non-polymeric materials which may be used as the matrix in the compositions of the invention include any material into or onto which the polyionic bioactive agent of the invention may be incorporated. Such non-polymeric materials may be biodegradable or non-biodegradable, but must be biocompatible. By way of example, useful non-polymeric materials include titanium, platinum, stainless steel, other biocompatible metal alloys, hydroxyapatite, tricalcium phosphate, cocoa butter, waxes, ceramic materials.

Other materials which may be used as the matrix in the compositions of the invention include, for example, cross-linked and non-cross-linked structural proteins, such as collagens (e.g. type I, type II, or type III collagen) or elastin.

The Polyionic Condensing Agent of the Composition of the Invention

The chemical identity of the polyionic condensing agent of the composition of the invention is not critical. Instead, it is important that the polyionic condensing agent have a charge that is opposite the charge of the polyionic bioactive agent of the composition and that, when the polyionic condensing agent and the polyionic bioactive agent are combined, the polyionic bioactive agent assumes a condensed form or conformation. Thus, when a polyanionic bioactive agent is used in the compositions and methods of the invention, a polycationic condensing agent should be used. Similarly, when a polycationic bioactive agent is used in the compositions and methods of the invention, a polyanionic condensing agent should be used. When a bioactive agent which has both positive and negative charges is used, the polyionic condensing agent should have a charge that is the opposite of the net charge of the bioactive agent. When a bioactive agent having a plurality of charged groups but having a net charge near neutrality is used, either a polyanionic or a polycationic condensing agent may be used.

The suitability of a polyionic condensing agent for use in combination with a given polyionic bioactive agent may be determined by combining the polyionic condensing agent and the polyionic bioactive agent and assessing a change in a relevant property of the polyionic bioactive agent. Relevant properties of the polyionic bioactive agent include, but are not limited to, nuclease susceptibility, protease susceptibility, hydrodynamic diameter, conformation, and susceptibility to oxidation. Furthermore, upon condensation, the geometric dimensions of polyionic bioactive agents may be significantly reduced, their charge may be neutralized, they may become more resistant to enzymatic degradation, they may become more resistant to nonspecific hydrolysis, and/or they may exhibit altered electrophoretic mobility. If combining the polyionic bioactive agent with the polyionic condensing agent reduces the nuclease susceptibility of the polyionic bioactive agent, reduces the proteolytic susceptibility of the polyionic bioactive agent, decreases the hydrodynamic diameter of the polyionic bioactive agent, causes the polyionic bioactive agent to assume a more geometrically compact conformation, or reduces the susceptibility of the polyionic bioactive agent to oxidation, then the polyionic condensing agent is suitable for use with the polyionic bioactive agent in the compositions and methods of the invention.

In various preferred embodiments, the polyionic bioactive agent is a nucleic acid such as DNA. Thus, in these embodiments, it is preferred that a polycationic condensing agent be used in the compositions and methods of the invention. The ability of a polycationic condensing agent to condense DNA or another nucleic acid or nucleic analog may be assessed using numerous methods known in the art. Effective amounts of such polycationic condensing agents may similarly be determined using these methods. For example, DNA condensation may be measured by comparing the kinetics in solution of condensed DNA and uncondensed DNA, and then further comparing the kinetics in the presence of a surfactant such as a detergent. It may also be measured by changes in the surface ζ-potential of the DNA in solution (Wolfert et al., 1996, Human Gene Therapy 7:2123–33), or by visualizing the DNA using an electron microscope (Laemmli, 1975, Proc. Natl. Acad. Sci. USA 72:4288–4292) or an atomic force microscope (Wolfert et al., 1996, Gene Therapy 3:269–273).

One preferred family of polycationic condensing agents is the polylysines. Polylysines consist of polypeptides of varying lengths, comprising lysine residues, which are positively charged at human physiological blood pH. The lysine residues can be D-lysine residues, L-lysine residues, or a mixture of the two enantiomers; poly-L-lysine is preferred. Polylysine has been demonstrated to be an efficacious DNA condensing agent (Laemmli, 1975, Proc. Natl. Acad. Sci. USA 72:4288–4292; Wolfert et al., 1996, Gene Therapy 3:269–273). The polylysines which are useful as polycationic condensing agents in the compositions and methods of the invention include all variants of polylysine, regardless of length, linear, branched, or cross-linked structure, conformation, isomerization, or chemical modification, that are capable of condensing DNA or other polyanionic bioactive agents. Exemplary chemical modifications include methylation (Bello et al., 1985, J. Biomol. Struct. Dyn. 2:899–913) and glycosylation (Martinez-Fong et al., 1994, Hepatology 20:1602–1608). Such modifications may be made before or after synthesis of the polylysine.

In alternative embodiments of the compositions and methods of the invention, the condensing agent is a polycationic polypeptide other than a polylysine. Several amino acids are known to be positively charged at human physiological blood pH. Among the naturally occurring amino acids, lysine, arginine, and histidine are positively charged in this pH range. Other, naturally occurring and synthetic, amino acids are positively charged in this pH range. Any of these amino acids can be polymerized into linear, branched, or cross-linked chains to generate polycationic polypeptides which are useful as polycationic condensing agents in the compositions and methods of the invention. Synthetic polypeptides may be produced by either chemical synthetic methods or recombinant methods. These polycationic condensing polypeptides may be homopolymers, such as polylysine, polyarginine, polyornithine, or polyhistidine, or they may be heteropolymers, such as proteins such as myelin basic protein.

One particularly useful group of polycationic condensing agents are the DNA-binding proteins. These proteins include those which bind DNA non-specifically, such as histones or sperm surface proteins (Lavitrano et al., 1992, Mol. Reprod. Dev. 31:161–169), or those which bind DNA specifically, such as transcription factors. DNA-binding proteins may be used as whole proteins or as peptide fragments that include the DNA-binding domain(s) of the protein. They may also be made synthetically, either as individual proteins or domains or as longer peptides consisting of repeating DNA-binding domains obtained from one or more DNA-binding proteins. Many other naturally-occurring polypeptides and proteins are polycationic, and are thus useful as polycationic condensing agents in the compositions and methods of the invention. As non-limiting examples of the use of other proteins as DNA condensing agents, Wadhwa et al (1995, Bioconj. Chem. 6:283–291) used low molecular weight glycopeptides as DNA condensing agents, Niidome et al. (1997, J. Biol. Chem. 272:15307–15312) used cationic amphiphilic alpha-helical oligopeptides with repeating sequences as DNA condensing agents, and Chen et al. (1994, Hum. Gene Ther. S:429–435) used galactosylated histones for gene delivery.

One skilled in the art will recognize that variants of all these different protein structures would also be expected to function as condensing agents. Such a skilled artisan would recognize the possibility of making conservative substitutions in the polypeptides that would not disturb the function as a condensing agent, including substitution with non-naturally-occurring amino acids, D-enantiomers of amino acids, or both. Indeed, virtually any polypeptide that is polycationic in nature is likely to function as a condensing agent, and the skilled artisan could ascertain the degree of condensing ability, as described herein, with merely routine experimentation.

Alternative polycationic condensing agents which may be used to condense DNA, other nucleic acids, and other polyanionic bioactive agents include elemental cations, particularly divalent cations such as $Mg^{2+}$ or $Ca^{2+}$. Such cations may, for example, be used in the form of salts, such as $MgCl_2$ or $CaCl_2$. Indeed, $Ca^{2+}$ in the form $Ca_3(PO_4)_2$ is one of the most commonly known and used agents for DNA condensation in preparation for naked DNA transfection. Other suitable elemental cations include $Co^{3+}$ (particularly in the form of cobalt hexamine, $Co(NH_3)_6^{3+}$, or cobalt pentamine), $La^{3+}$, $Al^{3+}$, $Ba^{2+}$ and $Cs^+$. These cations are generally used in the form of a salt, particularly halide salts such as chloride and bromide salts, but other salts may be used as well, as will be appreciated by the skilled artisan in view of the present disclosure.

The polycationic condensing agents which are useful in the compositions and methods of the present invention are not limited to the polycations listed above, or any other particular set of polycationic molecules. Any polycationic molecule that has the property of condensing DNA or other polyanionic bioactive agents is within the scope of the polycationic condensing agents of the present invention. Thus, for example, such commonly known polycationic DNA condensing agents as polybrene, spermine, spermidine, prolamine (including prolamine sulfate and other salts; Sorgi et al., 1997, Gene Therapy 4:961–968), polyethylenimine, putrescine, cadaverine, hexamine, and other polyamines, and derivatives thereof, such as partially or fully methylated versions, are all polycationic condensing agents which are useful in the compositions and methods of the present invention. In addition, two or more of the polycationic condensing agents may be used in combination to condense the polyanionic bioactive agent of the invention.

The polycationic condensing agent may optionally have other molecules bound to them, such as, for example, a polypeptide or a linker for the attachment of a polypeptide. In particular, this polypeptide may be an agent that imparts to the composition of the invention the ability to target and bind specific tissues or cells, allow them be retained at the administration site, etc., as described herein. The polypeptide may be attached, for example, by a disulfide linkage or by the well-known biotin-avidin system. If the condensing agent is also a polypeptide, the two molecules may also be part of the same peptide chain, bound by a standard peptide bond. For example, it may be desirable to create hybrid molecules combining a receptor-specific molecule and the condensing agent (e.g. Sosnowski et al., 1996, J. Biol. Chem. 271:33647–33653). The receptor-specific molecule may, for example, be an antibody, a hormone, a growth factor, or any other molecule which imparts target specificity.

When a polycationic bioactive agent is used in the compositions and methods of the invention, a polyanionic condensing agent should also be used in those compositions and methods. A preferred class of polyanionic condensing agents are nucleic acids, including DNA. The high negative charge density of nucleic acids at human physiologic blood pH makes nucleic acids favorable agents for condensing bioactive agents having a high positive charge density. Nucleic acids may be used to condense bioactive agents such as proteins in either a nucleotide-sequence-specific manner or in a sequence non-specific manner. It is well known that certain proteins bind to nucleic acids only if those nucleic acids have a particular sequence, and that many of these proteins exhibit an altered conformation upon binding to a nucleic acid having that sequence. Furthermore, certain proteins exhibit altered susceptibility to proteolysis following binding of the protein to a particular nucleic acid sequence. It is also well known that certain proteins bind to nucleic acids in a manner that is not dependent upon the nucleotide sequence of the nucleic acid, and that many of such proteins exhibit altered conformation or proteolytic susceptibility following such binding. Therefore, nucleic acids may be used to condense numerous protein bioactive agents for use in the compositions of the invention.

Other polyanionic condensing agents which are contemplated for use in the compositions and methods of the invention include naturally-occurring proteins, such as those described herein, which have a net negative charge at human physiologic blood pH and homopolymers and heteropolymers comprising a plurality of amino acid residues which are negatively charged in this pH range. Exemplary amino acid residues which are negatively charged in this pH range include aspartate and glutamate, although the use of non-naturally-occurring and chemically modified amino acid residues is also contemplated. Polymers having a plurality of negatively charged groups may also be effectively used as polyanionic condensing agents.

The Implantable Device of the Invention

The compositions of the invention may be used to make, to make a part of, to coat, or to coat a part of substantially any device which is to be applied to a surface of the body of an animal or which is to be inserted within the body of an animal. The implantable device may be one which is made and used for the sole purpose of delivering the composition of the invention to the animal, or the device may be one which is applied to the surface of or inserted within the body of the animal for a purpose other than merely delivering the composition of the invention to the animal. By way of example, the implantable device may be a plurality of microspheres which consist of the composition of the invention and which are implanted into the body animal for the sole purpose of delivering the polyionic bioactive agent to the animal. Further by way of example, the implantable device may be a cardiovascular stent coated with the composition of the invention; the stent is implanted within an artery of an animal both to maintain the patency of the artery and to deliver the composition of the invention to the intimal tissue of the artery or to other tissue.

The compositions and methods of the invention may be used to coat all or part of virtually any medical device. The coated devices provide a convenient means for local administration of the polyionic bioactive agent of the composition. For example, the compositions of the invention can be used to coat degradable and non-degradable sutures, orthopedic protheses such as supporting rod implants, joint protheses, pins for stabilizing fractures, bone cements and ceramics, tendon reconstruction implants, prosthetic implants, cardiovascular implants such as heart valve prostheses, pacemaker components, defibrillator components, angioplasty devices, intravascular stents, acute and in-dwelling catheters, ductus arteriosus closure devices, implants deliverable by cardiac catheters such as atrial and ventricular septal defect closure devices, urologic implants such as urinary catheters and stents, neurosurgical implants such as neurosurgical shunts, ophthalmologic implants such as lens prosthesis, thin ophthalmic sutures, and corneal implants, dental prostheses, internal and external wound dressings such as bandages and hernia repair meshes, and other devices and implants, as will be readily apparent to the skilled artisan.

In a particularly preferred embodiment, the invention provides sutures coated with the composition of the invention, especially sutures coated with a polymeric matrix containing a nucleic acid that stimulates wound healing in vivo, the nucleic acid being present in a condensed form in at least the outermost portion of the polymeric coating. Sutures which may be coated in accordance with the methods and compositions of the present invention include any suture of natural or synthetic origin. Typical suture materials include, by way of example and not limitation, silk, cotton, linen, polyolefins such as polyethylene and polypropylene, polyesters such as polyethylene terephthalate, homopolymers and copolymers of hydroxycarboxylic acid esters, plain or chromicized collagen, plain or chromicized catgut, and suture substitutes such as cyanoacrylates. The sutures may take any convenient form such as braids or twists, and may have a wide range of sizes, such as are commonly employed in the art.

Methods of Making the Compositions of the Invention

To make the compositions of the invention, it is necessary to provide a matrix which comprises the polyionic bioactive agent of the invention at at least the exterior portion of the matrix. The polyionic bioactive agent may be present only on the surface of the matrix, only within a layer of the matrix which includes the surface of the matrix, or throughout the matrix. The exterior portion of the matrix is contacted with a polyionic condensing agent having a charge opposite that of the polyionic bioactive agent. When the polyionic condensing agent contacts the polyionic bioactive agent, at least most of the polyionic bioactive agent assumes a condensed form at at least the exterior portion of the matrix. The matrix may be contacted with the polyionic condensing agent in such a manner and for such a period of time that the polyionic bioactive agent, if any, at an interior portion of the matrix also assumes a condensed form, or in such a manner and for such a period of time that the polyionic bioactive agent, if any, at the interior portion of the matrix remains in a non-condensed form. It is understood that the composition of the polyionic condensing agent, the solvent in which the polyionic condensing agent is dissolved or suspended, the duration for which the matrix and the polyionic condensing agent are contacted, the temperature at which the matrix and the polyionic condensing agent are contacted, and other conditions which are apparent to the skilled artisan in view of the present disclosure, may be varied to control whether the polyionic bioactive agent at an interior portion of the matrix assumes a condensed form or not.

The method by which the matrix comprising the polyionic bioactive agent at at least the exterior portion thereof is not critical. Substantially any method of generating this composition may be used (e.g. Mathiowitz et al., 1997, Nature 386:410–414). Preferably, the matrix comprising the polyionic bioactive agent is provided in the form of microspheres or nanospheres. Methods for generating microspheres and nanospheres comprising polyionic bioactive agents such as DNA have been described (e.g. Song et al., 1997, J. Controlled Release 43:197–212; Duguid et al., 1998, Biophys. J. 74:2802–2814; Maruyama et al., 1997, Bioconj. Chem. 8:735–742; Jones et al., 1997, Vaccine 15:814–817; Mathiowitz et al., 1997, Nature 386:410–414). However, the matrix may also be provided in other forms, including as a bulk matrix which can be sliced, cut, shaped, or otherwise manipulated prior to contacting the matrix with the polyionic condensing agent as described herein.

The polyionic condensing agent of the invention is contacted with at least the exterior portion of the matrix. The polyionic condensing agent may be present in the form of a solid, a powder, a liquid, a solution, a suspension, droplets, and other similar forms, depending upon the chemical identity and properties of the polyionic condensing agent. For example, when the matrix comprises DNA and the polyionic condensing agent is polylysine, the matrix may be contacted with a suspension of polylysine in water or in a suitable buffer (e.g. Tris-chloride, pH 7.2 buffer or a buffer comprising 50 millimolar Tris and 10 millimolar EDTA at pH 7.4).

The matrix may be contacted with the polyionic condensing agent only momentarily, or the two may be contacted for a prolonged period of minutes, hours, days, or even weeks.

The amount or concentration of polyionic condensing agent that is contacted with the matrix may be varied to control the proportion of the polyionic bioactive agent that assumes a condensed form in the exterior portion of the matrix. Preferably, the polyionic condensing agent is used in significant excess, on either a molar or a by-weight basis, with respect to the polyionic bioactive agent, with the result that at least most, and more preferably substantially all, of the bioactive agent at the exterior portion of the matrix assumes a condensed form. The polyionic condensing agent is added in an amount that is effective to condense at least most of the polyionic bioactive agent in the exterior portion of the matrix. The effective amount will depend on the precise composition of the matrix, the identity of the polyionic bioactive agent, and the identity of the polyionic condensing agent. Typically, the amount of the polyionic condensing agent which is used is an amount such that molar quantity of ionic sites on the condensing agent is equal to or greater than the molar quantity of ionic sites on the bioactive agent at the exterior portion of the matrix. The ratio of ionic sites on the condensing agent to ionic sites on the bioactive agent is preferably between about 1 and about 20, more preferably between about 5 and about 15, and even more preferably about 10, although higher ratios are also useful.

The amount of condensing agent may also be expressed in terms of the concentration ratio relative to the bioactive agent. The ratio of condensing agent: bioactive agent is preferably in the range of about 0.1:1 to about 20:1, more preferably in the range of about 0.2:1 to about 1:1, and even more preferably in the range of about 0.3:1 to about 0.5:1. Alternatively, the amount of condensing agent may also be expressed in terms of the concentration ratio relative to the matrix. The ratio of condensing agent:matrix is preferably in the range of about 1:400 to about 1:20, more preferably in the range of about 1:300 to about 1:40, and even more preferably in the range of about 1:200 to about 1:50. The amount of condensing agent may alternatively be expressed as a percentage of the volume of the aqueous phase in which it is dissolved or suspended; preferred percentages are in the range of about 0.1% (w/v or v/v) to about 30%, more preferably about 1% to about 20%, even more preferably about 2% to about 8%.

When poly-L-lysine having a molecular weight in the range from 1000 to 4000 is used as the polyionic condensing agent in conjunction with DNA-containing microspheres, for example, the effective amount of poly-L-lysine is preferably between about 0.1 and about 15 milligrams per milliliter, more preferably between about 0.2 and about 5 milligrams per milliliter, still more preferably between about 0.5 and about 2 milligrams per milliliter, and even more preferably about 2 milligrams per milliliter.

When a salt of an elemental cation is used as the polyionic condensing agent, for example $MgCl_2$ or $CaCl_2$, the effective amount is preferably between about 8 millimolar and about 1 molar cation, and more preferably between about 8 millimolar and about 0.5 molar.

After contacting the matrix with the polyionic condensing agent and thereby condensing at least most of the polyionic bioactive agent in the exterior portion of the matrix, any excess polyionic condensing agent may be removed from the matrix, for example by rinsing the matrix with a solvent in which the polyionic condensing agent can be dissolved or suspended, or the excess condensing agent may be left in place on the matrix. When the polyionic condensing agent is one which, when delivered to an animal tissue, can induce an unfavorable biological response in the tissue, it is preferred that any excess condensing agent be removed from the matrix.

Implantable devices such as particles, patches, and bulk materials may be fashioned from the composition of the invention either by making such an implantable device entirely from the composition of the invention (e.g. an implantable particle consisting of the composition of the invention), or by separately making the implantable device and coating all or a portion thereof with the composition of the invention (e.g. a stainless steel vascular stent having a polymeric coating comprising the composition of the invention. When the matrix of the composition of the invention comprises a polymer, the composition may be made by providing monomers of the invention and thereafter polymerizing the monomers (e.g. coating a device with matrix monomers and the polyionic bioactive agent and thereafter polymerizing the monomers and condensing at least most of the bioactive agent in the exterior portion of the matrix). Alternately, when the matrix of the composition of the invention comprises a polymer, the composition may be made by providing the polymer dissolved or suspended in a solvent and thereafter removing the solvent (e.g. coating a device with a solvent in which a polymer and the polyionic bioactive agent are dissolved or suspended and thereafter removing the solvent and condensing at least most of the bioactive agent in at least the exterior portion of the polymeric matrix). When implantable polymeric particles are made, the particles may either be synthesized as discrete particles, or the particles may be made by generating a bulk material and subsequently cutting, crushing, or grinding the bulk material to yield particles. Where bulk material comprising the composition of the invention is made, it is contemplated that the bulk material may be cut, shaped, sliced, or otherwise fashioned to be adapted to a cavity or other bodily structure of an animal into which the composition is to be implanted. Implantation of slices of a bulk polymeric material comprising an anticancer agent near the site of a brain tumor in a human patient is known (Fung et al., 1988, Cancer Res. 58:672–684; Brem et al., 1995, J Neurooncol. 26:111–123). By way of example, the bulk polymeric material may comprise a nucleic acid which is either an expression vector encoding an oncogene or an antisense oligonucleotide directed against an oncogene. Exemplary oncogenes include, but are not limited to abl, akt2, apc, bcl2α, bcl2β, bcl3, bcr, brcal, brca2, cbl, ccnd1, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf1, wnt1, wnt2, wt1, and yes1.

Implantation of slices, particles, needles, strips, or other geometrical forms generated from a bulk material comprising the composition of the invention is contemplated. The polyionic bioactive agent of the composition may be condensed either prior to reformation of the bulk material (e.g. by contacting the bulk material with the polyionic condensing agent of the invention and thereafter reforming the bulk material) or after reformation of the bulk material (e.g. by making particles, slices, cubes, etc. from the bulk material, and thereafter contacting the particles, slices, or cubes with the polyionic condensing agent of the invention).

Methods of Delivering a Polyionic Bioactive Agent to an Animal Tissue

The compositions of the invention are useful for delivering a polyionic bioactive agent to an animal tissue, preferably a soft tissue of the animal. The bioactive agent is delivered to the tissue by placing a composition of the invention which comprises the bioactive agent in fluid communication with the animal tissue. The composition may, for example, be in the form of implantable particles or an implantable device having a surface coated with the composition of the invention. By providing the composition in fluid communication with the tissue in a form in which at least most of the polyionic bioactive agent at the exterior portion of the matrix of the composition is in a condensed form, nucleolytic or proteolytic degradation of the bioactive agent is minimized. Furthermore, delivery of the bioactive agent in a condensed form can extend the period of time over which the bioactive agent is released from the matrix of the composition, resulting in sustained-release-type delivery of the bioactive agent to the tissue. The compositions of the invention are thus particularly useful in instances in which sustained delivery of the bioactive agent is desired.

In one preferred embodiment of the method of delivering a polyionic bioactive agent to an animal tissue, the matrix of the composition is a stainless steel vascular stent and the polyionic bioactive agent is a nucleic acid selected from the group consisting of an expression vector encoding an anti-restenotic protein and an anti-restenotic antisense oligonucleotide. The expression vector may, for example, encode an anti-restenotic protein selected from the group consisting of TPA, TGF-β, FGF, Rb, p21, and TK. The anti-restenotic antisense oligonucleotide may, for example, be selected from the group consisting of a c-myb antisense oligonucleotide, a c-myc antisense oligonucleotide, and a PCNA antisense oligonucleotide. The polyionic bioactive agent may be present on a surface of the stent together with the polyionic condensing agent of the invention, or it may be present on a surface of the stent in the form of a coating matrix (e.g. a polymer coating a surface of the stent) in which at least most of the bioactive agent in the exterior portion of the matrix is present in a condensed form.

In another embodiment of the method of delivering a polyionic bioactive agent to an animal tissue, the matrix of the composition comprises both an exterior portion and an interior portion. At least most, and preferably all or substantially all, of the polyionic bioactive agent of the invention in the exterior portion of the matrix is present in a condensed form. All, substantially all, less than most, or even none of the polyionic bioactive agent in the interior portion of the matrix may be present in a condensed form. By way of example, microspheres or nanospheres may be formed, using methods described herein or by others, whereby the microspheres or nanospheres comprise a polyionic bioactive agent suspended in a polymeric matrix. The interior portion of the micro/nanospheres may comprise the polymeric matrix, or it may comprise a solvent in which the polymeric matrix may be suspended or dissolved. After forming the micro/nanospheres, the micro/nanospheres are treated with a polyionic condensing agent which condenses at least most of the polyionic bioactive agent molecules which are present on the exterior surface of the micro/nanospheres, but which does not penetrate into the interior portion of the micro/nanospheres. Thus micro/nanospheres are generated comprising an exterior portion at which at least most of the bioactive agent is in a condensed form and an interior portion at which substantially none or none of the bioactive agent is present in a condensed form.

In another preferred embodiment of the method of delivering a polyionic bioactive agent to an animal tissue, the matrix of the composition is a suture coated with the composition of the invention. In this embodiment, the composition comprises a polymeric matrix and the polyionic bioactive agent is a nucleic acid expression vector encoding a wound healing therapeutic protein. The wound healing therapeutic protein may, for example, be selected from the group consisting of TGF-β, FGF, PDGF, IGF, M-CGF, BMP, GH, and PTH. Preferably, the suture comprises a plurality of layers of the polymeric matrix comprising the polyionic bioactive agent, wherein at least most of the polyionic bioactive agent in at least the exterior portion of the outermost polymeric matrix layer of the suture is present in a condensed form. Meshes (e.g. hernia repair meshes) and wound dressings (e.g. bandages) which comprise, which consist, or which are coated with the composition of the invention as described in this embodiment are also contemplated.

According to this method of the invention, the composition of the invention must be placed in fluid communication with the animal tissue to which the polyionic bioactive agent is to be delivered. The composition, by itself or attached to an implantable device, may be implanted into the animal at a location at which a liquid (e.g. a body fluid such as blood, lymph, cerebrospinal fluid, a mucosal secretion, stomach or intestinal contents, or amniotic fluid) contacts both the implanted composition and the tissue to which the polyionic bioactive agent is to be delivered. Preferably, the composition is implanted at a body location which is geometrically close to the tissue to which delivery is desired, preferably within a few centimeters, a few millimeters, or even in contact with the desired tissue.

The method of placing the composition, or a particle or device comprising the composition, in fluid communication with the tissue to which the bioactive agent is to be delivered is not critical. Virtually any method may be used which will result in placement of the composition in fluid communication with the tissue. By way of example, depending on the location of the tissue, the composition may be administered orally, injected, placed into an incision made in the animal body, embedded in an animal tissue (e.g. a vascular tissue undergoing balloon angioplasty) by stretching the tissue and pressing particles of the composition against the tissue, infusing the composition, sealing an incision made in the animal body using a suture, staple, or other device comprising or coated with the composition, or by applying the composition topically to an animal tissue.

The invention encompasses the preparation and use of pharmaceutical compositions comprising the composition of the invention. Such a pharmaceutical composition may consist of the composition alone, in a form suitable for administration to a subject, or the pharmaceutical composition may comprise the composition or a particle or device coated with the composition of the invention combined with one or more pharmaceutically acceptable carriers, one or more additional ingredients, or some combination of these. Administration of one of these pharmaceutical compositions to a subject is useful for delivering the polyionic bioactive agent of the composition to the subject, as described elsewhere in the present disclosure.

As used herein, the term "pharmaceutically acceptable carrier" means a chemical composition with which the active ingredient may be combined and which, following the combination, can be used to administer the active ingredient to a subject.

The formulations of the pharmaceutical compositions described herein may be prepared by any method known or hereafter developed in the art of pharmacology. In general, such preparatory methods include the step of bringing the composition of the invention into association with a carrier (e.g. water or phosphate-buffered saline) or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include microspheres, nanospheres, projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the composition of the invention. The amount of the composition is generally equal to an amount which contains a desirable dosage or amount of the polyionic bioactive agent for delivery to the subject or a convenient fraction of such a dosage such as, for example, one-half or one-third of such a dosage.

The relative amounts of the composition, the pharmaceutically acceptable carrier, and any additional ingredients in a pharmaceutical composition of the invention will vary, depending upon the identity, size, and condition of the subject treated and further depending upon the route by which the composition is to be administered. By way of example, the pharmaceutical composition may comprise between 0.1% and 100% (w/w) of the composition of the invention.

In addition to the composition of the invention, a pharmaceutical composition of the invention may further comprise one or more additional pharmaceutically active agents. Particularly contemplated additional agents include ganciclovir (particularly in conjunction with either TK protein or an expression vector comprising a nucleic acid which encodes TK) or an activator or inducer of an activatable or inducible promoter (e.g. tetracycline). For example, a composition of the invention may comprise a matrix, ganciclovir, and an expression vector comprising a nucleic acid which encodes TK. Administration of the composition to a body cavity of an animal causes localized transformation of cells which are in fluid communication with the composition and uptake of ganciclovir by those cells. Proliferating transformed cells are killed by the enzymatic activity of TK upon ganciclovir within those cells. The present inventors have demonstrated the operability of such a composition using a matrix comprising an expression vector comprising a nucleic acid which encodes TK and as little as 20 micrograms of ganciclovir (as opposed to the normal systemic dose of 25 milligrams per kilogram body weight).

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the composition of the invention or a predetermined amount of the polyionic bioactive agent of the invention. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the composition of the invention may, for example, be made by compressing or molding the composition, optionally with one or more additional ingredients. Compressed tablets may be prepared by compressing, in a suitable device, the composition of the invention in a free-flowing form such as a microspherical or nanosphereical powder or granular preparation, optionally mixed with one or more of a binder, a lubricant, an excipient, a surface active agent, and a dispersing agent. Molded tablets may be made by molding, in a suitable device, a mixture of the composition of the invention, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the composition of the invention. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the composition of the invention may be made using a physiologically degradable composition, such as gelatin. Such hard capsules comprise the composition of the invention, and may further comprise additional ingredients including, for example, an inert solid diluent such as calcium carbonate, calcium phosphate, or kaolin.

Soft gelatin capsules comprising the composition of the invention may be made using a physiologically degradable composition, such as gelatin. Such hard capsules comprise the composition of the invention, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the composition of the invention in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the composition of the invention in aqueous or oily solvents may be prepared in substantially the same manner as liquid suspensions. Liquid solutions of the pharmaceutical composition of the invention may comprise each of the components described with regard to liquid suspensions. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the composition of the invention with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the composition of the invention with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the composition of the invention with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

Vaginal preparations of the composition of the invention may also be used for administration in utero of the polyionic bioactive agent of the invention to an ovum, embryo, fetus, or to a neonate during birth. Such preparations are preferably placed in the uterus of the woman bearing the ovum, embryo, fetus, or neonate, although such preparations may also be placed cervically or vaginally.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, by application using a device (e.g. a balloon angiocatheter) inserted at one site in a blood vessel of an animal and physically urged along the vessel to a second site in the blood vessel of the animal, by administration of the composition using a wound dressing (e.g. a bandage, a suture, or a hernia repair mesh) comprising the pharmaceutical composition, and the like. In particular, parenteral administration is contemplated to include, but is not limited to, subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the composition of the invention combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. microspherical or nanospherical powder or granular) form for reconstitution with a suitable vehicle (e.g. sterile pyrogen-free water) prior to parenteral administration of the reconstituted composition. Use of a double-balloon or 'sweating' balloon type of angiocatheter to deliver a pharmaceutical composition of the invention to the intimal surface of a blood vessel of an animal is contemplated. Also contemplated is delivery of the polyionic bioactive agent of the invention using a pharmaceutical composition comprising a wound dressing which comprises the composition of the invention.

The pharmaceutical compositions may be prepared, packaged, or sold in the form of a sterile injectable aqueous or oily suspension or solution. This suspension or solution may be formulated according to the known art, and may comprise, in addition to the composition of the invention, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the composition of the invention in bulk form, in particulate form, in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) of the composition of the invention, although the concentration of the active ingredient may be as high as the solubility limit of the active ingredient in the solvent. Formulations for topical administration may further comprise one or more of the additional ingredients described herein. Preferably, the composition of the invention is in a microspherical or nanospherical form when it is used to generate a pharmaceutical composition for topical administration, as these forms may be more efficiently taken up by animal tissues.

A pharmaceutical composition of the invention may be prepared, packaged, or sold in a formulation suitable for pulmonary administration via the buccal cavity. Such a formulation may comprise dry particles which comprise, which consist of, or which are coated with the composition of the invention and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the composition of the invention dissolved or suspended in a biocompatible, low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the pharmaceutical composition, and the composition of the invention may constitute 0.1 to 20% (w/w) of the pharmaceutical composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the composition of the invention in the form of droplets of a solution or suspension of the composition. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the composition of the invention and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the composition of the invention, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) of the composition of the invention, the balance comprising an orally dissolvable or degradable composition and, optionally, one or more of the additional ingredients described herein. Alternately, formulations suitable for buccal administration may comprise a powder or an aerosolized or atomized solution or suspension comprising the composition of the invention. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the composition of the invention in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

It is understood that the ordinarily skilled physician or veterinarian will readily determine and prescribe an effective amount of the composition of the invention for delivery to the subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the identity of the polyionic bioactive agent of the invention, the activity of the bioactive agent, the estimated efficiency of uptake of the bioactive agent by the subject, the age, body weight, general health, gender, and diet of the subject, the time of administration, the route of administration, the rate of excretion, any drug combination, and the severity of the condition being treated.

The animal tissue to which the polyionic bioactive agent of the invention is delivered is not critical, except insofar as the identity of the tissue corresponds to the condition to be treated in the animal. By way of example, prevention or amelioration of restenosis in an animal generally requires delivery of the bioactive agent to at least a portion of a blood vessel of the animal, and promotion of wound healing in an animal generally requires delivery of the bioactive agent to the wounded tissue. An animal tissue may be treated either in situ (i.e. while the tissue remains a part of the animal body), or the tissue may be treated in vitro (i.e. after removing the tissue from the animal body, optionally before returning the tissue to the animal body or treating a tissue which has been cultured since removing the tissue from the animal body).

The Kits of the Invention

The invention includes a variety of kits which are useful for making and using the compositions of the invention.

In one embodiment of a kit of the invention, the kit comprises the matrix of the composition of the invention and an instructional material which describes combining the matrix with a polyionic bioactive agent and condensing the bioactive agent. The matrix may, for example, be provided in the form of a non-polymer matrix which may be mixed or coated with the bioactive agent, monomers which may be combined with the bioactive agent and thereafter polymerized, monomers which may be polymerized and thereafter combined with the bioactive agent, a polymeric matrix into or onto which the bioactive agent may be incorporated, and the like. The instructional material may, for example, describe how to use the components of the kit, optionally with commercially available reagents or with a polyionic bioactive agent of the user's design, to generate a composition of the invention. Alternately, or in addition, the instructional material may describe how to use the composition of the invention to deliver a polyionic bioactive agent to an animal tissue, preferably a soft tissue of the animal. The kit may optionally comprise one or more of the polyionic bioactive agent of the invention, the polyionic condensing agent of the invention, and a solvent in which the matrix of the invention may be dissolved or suspended. In an alternate embodiment of the kit of the invention, the kit comprises the composition of the invention and one or more of an instructional material for administering the composition to an animal tissue, a device for administering the composition of the invention to an animal tissue, and pharmaceutical carrier for combination with the composition of the invention prior to administering the composition to an animal tissue.

The Nucleic Acid Storage Method of the Invention

The invention also includes a method of storing a nucleic acid. The method, as described herein, is particularly amenable for long-term storage of a nucleic acid. This method is useful for, among other things, collecting nucleic acid samples in situations in which standard laboratory nucleic acid storage methods (e.g. low temperature storage or storage in the presence of one or more nuclease inhibitors such as EDTA) cannot be implemented immediately following collection of the sample. According to this method of the invention, a nucleic acid sample is suspended in a matrix and the matrix is contacted with a polycationic condensing agent, such as one of those described herein. At least most of the nucleic acid in the exterior portion of the matrix, and preferably substantially all of the nucleic acid in the matrix, assumes a condensed form. The matrix may be contacted with the polycationic condensing agent after combining the matrix with the nucleic acid, or the polycationic condensing agent, the matrix, and the nucleic acid may be combined at the same time. In an alternate embodiment of this method, the matrix is coated with or embedded in a shell or other bulk form of a material which is relatively impervious to agents which cause nucleic acid degradation. Preferably, the material does not permit water, oxygen, or both to pass through the material, such as a metallic or polymeric material. By embedding or coating the matrix in such a material, nucleic acid degradation is minimized, particularly because much or all of the nucleic acid present in the matrix is in a condensed form, which renders it further resistant to degradation. Preferably the material which is used to coat or embed the matrix may be dissolved or otherwise removed from the matrix without causing degradation of the nucleic acid. By way of example, the material may be a polymer which can be dissolved or suspended in a solvent in which the nucleic acid is stable.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, a "polyionic bioactive agent" includes any substance that interacts with a biological element and that has a plurality of charged groups at the physiological pH of human blood (i.e. at about pH 7.4). Polyionic bioactive agents include substances such as dyes or labeling proteins which are primarily used to facilitate identification or visualization of biological structures or functions, as well as therapeutic molecules and molecules which are normal components of cells. Nucleic acids, nucleic acid analogs, polyionic proteins, and polyamines are non-limiting examples of polyionic bioactive agents.

By "nucleic acid" is meant any homopolymer or heteropolymer of deoxyribonucleosides, ribonucleosides, or nucleoside analogs. The nucleotide analogs may be any compound known in the art to be or subsequently discovered to be useful as a structural or functional analog of a ribonucleoside or a deoxyribonucleoside. Nucleotide analogs include, but are not limited to nucleotides comprising bases other than the five biologically occurring bases (adenine, guanine, thymine, cytosine and uracil). The monomers of the nucleic acid may be connected by phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages.

A nucleic acid "expression vector" is a nucleic acid which encodes an RNA or protein product which is formed upon transcription or upon transcription and translation of the nucleic acid. RNA expression vectors which can be directly translated to generate a protein product, or which may be reverse transcribed and either transcribed or transcribed and translated to generate an RNA or protein product, respectively, are also included within this definition.

A "transformation vector" is a nucleic acid or a nucleic acid-containing vector which, when provided to the interior of a cell, causes the cell to express an RNA or protein product encoded by the nucleic acid. RNA-containing vectors which, when provided to the interior of a cell, causes the cell to express an RNA, DNA, or protein product encoded by the RNA are also included within this definition.

A "transcribable vector" is a nucleic acid-containing vector which comprises a component of a virus, whereby, by the action of the virus component, the vector is enabled to enter a cell, to integrate its nucleic acid into the genome of the cell, or to transcribe, translate, or reverse-translate its nucleic acid in the cell.

A "transfection vector" is a DNA molecule having a transcriptional start site and any promoter/regulatory sequence which is necessary to enable an RNA molecule to be generated by transcription thereof or an RNA molecule having any promoter/regulatory sequence which is necessary to enable generation of a DNA molecule by reverse transcription thereof.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "ribozyme" is an RNA molecule, or a molecule comprising an RNA molecule and a polypeptide molecule, which is capable of specifically catalyzing a chemical reaction, in a manner analogous to enzymatic catalysis.

An "antisense oligonucleotide" is a nucleic acid molecule (e.g. DNA, RNA, or a polymer comprising one or more nucleotide analogs), at least a portion of which is complementary to a nucleic acid which is present in a cell. The antisense oligonucleotides of the invention preferably comprise between about twelve and about fifty nucleotides. More preferably, the antisense oligonucleotides comprise between about fourteen and about thirty nucleotides. Most preferably, the antisense oligonucleotides comprise between about sixteen and about twenty-one nucleotides. The antisense oligonucleotides of the invention include, but are not limited to, phosphorothioate oligonucleotides and other modifications of oligonucleotides, as described herein. Methods for synthesizing oligonucleotides, phosphorothioate oligonucleotides, and otherwise modified oligonucleotides are well known in the art (U.S. Pat. No. 5,034,506; Nielsen et al., 1991, Science 254: 1497), and each of these types of modified oligonucleotides in included within the scope of the invention.

A "viral fragment" means at least a portion of a nucleic acid which is a component of a naturally-occurring virus.

A "gene fragment" means at least a portion of a nucleic acid which, alone or in conjunction with other operably linked nucleic acids, constitutes a gene.

A "matrix" is any material with which a polyionic bioactive agent may be associated, for example by dissolution or suspension therein, by deposition thereon, or by ionic, covalent, or non-covalent bonding thereto.

The "exterior portion" of a matrix is a portion of the matrix which is capable of contacting a solvent in which the matrix is suspended or in which a device or particle coated with the matrix is suspended or immersed. It is understood that, in instances in which multiple layers of matrix are present, the "exterior portion(s)" of the matrix can refer only to the outermost portion of the outermost layer of the matrix (i.e. the last-deposited layer) or to the outermost portion of each layer of the matrix, with respect to the first-deposited layer. The exterior portion includes the exterior surface of the matrix and optionally further includes a portion of the matrix which is located near the exterior surface but which does not normally contact a solvent in which the matrix is suspended until the matrix has degraded. Thus defined, the exterior portion of the matrix can include the entire matrix.

A compound is present "at" the exterior portion of a matrix if the compound is present on the exterior surface of the matrix, within the matrix at a position which is located near the exterior surface but which does not normally contact a solvent in which the matrix is suspended until the matrix has degraded, or both.

The "exterior surface" of a matrix, device, particle, or surface is the surface or portion of a surface which contacts a solvent in which the matrix, device, particle, or surface is immersed.

A compound is present "substantially only on the exterior surface" of a matrix if at least most of the compound is present on the exterior surface of the matrix and no more than less than most of the compound is present in an interior portion of the matrix. Preferably, at least 75%, preferably at least 90%, and more preferably at least 99% of the compound is present on the exterior surface of the matrix, and less than 25%, preferably less than 10%, and more preferably less than 1% is present at an interior portion of the matrix.

The "interior portion" of a matrix is a portion of the matrix which does not contact a solvent in which the matrix is suspended or in which a device or particle coated with the matrix is suspended or immersed, at least until the matrix has at least partially biodegraded. It is understood that, in instances in which multiple layers of matrix are present, the "interior portion(s)" of the matrix can refer only to the innermost portion of the innermost layer of the matrix (i.e. the first-deposited layer) or to the inner portion of each layer of the matrix, with respect to the first-deposited layer. The interior portion of the matrix does not include the exterior surface of the matrix, but may include any and all parts of the matrix that are not exposed on the exterior surface.

A material is "biocompatible" with respect to an animal if the presence of the material in the animal is not injurious to the animal. By way of example, a biocompatible material does not induce an immune response to the material when the material is implanted in the body of an animal.

A material is "biodegradable" if the material undergoes decomposition when contacted with a biological system such upon implantation into an animal. The decomposition may be evidenced, for example, by dissolution, depolymerization, disintegration, or by another chemical or physical change whereby the bulk of the material in the biological system is reduced over time. Such decomposition may be, but is not necessarily, catalyzed by a component of the biological system (e.g. an enzyme).

A material is "in fluid communication" with a tissue if the material is in contact with a fluid which normally contacts the tissue, either in vitro or in vivo. Examples of materials in fluid communication with a tissue include a material deposited, suspended, or dissolved in a tissue culture medium in which the tissue is maintained, a material deposited, suspended, or dissolved in a body fluid which normally contacts the tissue in an animal, and a material which physically contacts the tissue. For the purposes of the present disclosure, embryonic and fetal tissues are considered to be "in fluid communication" with materials which physically contact the embryo or fetus, with materials which are deposited, suspended, or dissolved in amniotic fluid which surrounds the embryo or fetus, and with materials which are deposited, suspended, or dissolved in uteral, cervical, or vaginal fluids of an animal which bears the embryo or fetus.

A device, particle, or surface is "coated" with a material if at least a part of a surface of the device or particle or at least a part of the surface has the material present at the exterior surface thereof.

A polyionic bioactive agent is present "in a condensed form" if the bioactive agent is covalently or non-covalently associated with a polyionic condensing agent having a charge opposite the charge of the bioactive agent and if the polyionic bioactive agent, in the condensing agent-associated form, exhibits at least one of lower susceptibility to proteolysis, lower susceptibility to nucleolysis, smaller hydrodyanamic diameter, more compact conformation, and lower susceptibility to oxidation than the same bioactive agent when not associated with the condensing agent.

As used herein, the term "polycationic condensing agent" and grammatical forms thereof generally refers to molecules having a plurality of positive charges, but may also include certain monovalent cations that, because of their size or for some other reason, are able to condense polyanionic bioactive agents such as DNA. A non-limiting list of polycationic condensing agents which are suitable for condensing polyanionic bioactive agents such as DNA may be found in Lasic (1997, In: *Gene Delivery*, Lipsows, Ed., CRC Press, Boca Raton, Florida, pp. 33–37 and 56–61).

A "particle" or "particulate formulation" of a matrix means a matrix having geometric dimensions compatible with injection, cellular ingestion, or mucous membrane penetration. Thus, such a matrix typically comprises, or preferably consists essentially of, spherical or ellipsoid particles having a maximal geometric dimension of about 50 microns, preferably less than about one micron, and more preferably, from about 100 nanometers to 500 nanometers.

A "bulk material" or "bulk formulation" of a matrix means a monolithic matrix, having geometric dimensions in excess of those compatible with injection, cellular ingestion, or mucous membrane penetration. Such bulk formulations typically have one or more geometric dimensions in excess of 50 microns in diameter. Bulk materials may, for example, be provided in the form of spheres, irregular shapes, sheets, needles, bars, and the like.

The "hydrodynamic diameter" of an object such as a molecule or a particle refers to the diameter of an imaginary sphere which is traced by rotating the object in all directions around its center of mass. The hydrodyanamic diameter can be thought of roughly as the 'effective size' of an object rotating rapidly in space or in solution. By way of example, the hydrodyanamic diameter of a sphere is the actual diameter of the sphere, and the hydrodynamic diameter of a rigid rod-shaped object is the length of the object along its longest axis (i.e. the length of the rod). For rigid objects, the hydrodynamic diameter is equal to the largest geometric dimension of the object, measured along a straight line.

The "number-weighted mean particle diameter" of a population of particles is represented by the formula $\{(\Sigma n_y \times D_y)/\Sigma n_y\}$, wherein $n_y$ represents the number of particles having the hydrodynamic diameter represented by $D_y$, and wherein the summations are performed for all values of $D_y$ that are present in the population.

The term "at least most" means more than half, as assessed on a numerical or by-weight basis.

The term "less than most" means less than half, as assessed on a numerical or by-weight basis.

An "implantable device" means a particle or other object which can be entirely or partially inserted into the body of an animal. Implantable devices thus include particles which, when applied topically to a surface of the animal body, are capable of being taken up by a tissue or cell of the animal. The means by which the particle or other object is inserted into the animal body is not critical, and includes, for example, swallowing, inhalation, injection, topical application, physical penetration, insertion into an incision made in the animal body, and the like.

A "DNA-binding protein" is a polypeptide which binds to a DNA molecule, and includes both polypeptides which bind to nucleic acids having a particular nucleotide sequence and polypeptides which bind non-specifically to DNA molecules.

A "wound healing therapeutic protein" is a protein which, when provided to a wounded tissue in an animal, promotes healing of the wounded tissue.

An "anti-restenotic protein" is a protein which, when provided to the site of an intimal vascular injury (e.g. following performance of a balloon angioplasty procedure at the site), prevents, inhibits, or alleviates restenotic injury at the site. The anti-restenotic protein may, for example, prevent migration of smooth muscle or other cells to the site, prevent proliferation of smooth muscle or other cells at the site, or cause smooth muscle or other cells to dissociate from the site.

An "anti-restenotic antisense oligonucleotide" is an antisense oligonucleotide which, when provided to the site of an intimal vascular injury, prevents, inhibits, or alleviates restenotic injury at the site.

An "oncogene" as used herein, includes both genes which are identified in the art as oncogenes and those which are identified as tumor suppressor genes. A distinguishing characteristic of both oncogenes and tumor suppressor genes is their association with control the processes of oncogenesis, metastasis, or apoptosis.

A "soft tissue" means a tissue which does not primarily consist of one or more precipitated inorganic minerals. By way of example, mammalian bones and teeth primarily consist of a variety of precipitated inorganic minerals, and are not soft tissues.

As used herein, an "instructional material" includes a publication, a recording, a diagram, or any other medium of expression which can be used to communicate the usefulness of the composition of the invention for delivering a polyionic bioactive agent according to the methods of the invention or which can be used to communicate a method of making or using a composition of the invention as described herein. The instructional material of the invention may, for example, be affixed to a container which contains the composition of the invention or be shipped together with a container which contains the composition. Alternatively, the instructional material may be shipped separately from the container with the intention that the instructional material and the composition be used cooperatively by the recipient.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

The experiments described in this Example demonstrate that the use of a polycationic condensing agent to condense DNA in at least the exterior portion a DNA-containing-polymer-coated object extended the period over which the DNA was released from the object at human physiological blood pH.

In this preparation, polylactic polyglycolic acid copolymer (50:50, molecular weight 59,000) was dissolved in chloroform to achieve a final concentration of 3% (w/v). 3 milliliters of this solutions were combined with 100 microliters of a suspension of plasmid DNA encoding beta-galactosidase (pNGLVlacZ; 10 mg/ml in pH 7.4, 0.05 molar Tris buffer, EDTA, 0.01 molar). The resulting emulsion was vortexed until a milky homogeneity was attained, and this emulsion then was then dip-coated onto the Vicry1™ (Ethicon—Johnson & Johnson, Somerville, N.J.) mesh. A series of coating/drying steps were required, with about 5 minutes drying time in between each step, until the entire coating was applied. The coated mesh was then dried in a dessicator under vacuum for 24 hours.

An identical polyester mesh was coated with the same PLGA emulsion containing DNA, but was subjected to the following further treatment. The identical polyester mesh was contacted for one hour with a solution which comprised 10 milligrams per milliliter of polylysine (3400 molecular weight), and then air-dried for about 24 hours.

Each of the non-polylysine-treated mesh and the polylysine-treated mesh were separately exposed to a buffer comprising 50 millimolar Tris and 40 millimolar EDTA pH 7.4 at 37° C. for up to eighteen days, and release of DNA from each of the two meshes was quantitated as described (Nygren et al., 1998, Biopolymers 46:39–51).

The results of the experiments described in this Example are depicted in FIGS. 1A and 1B. FIG. 1A is a graph which represents release of DNA from non-polylysine-treated mesh. In FIG. 1A, the digits following "Vicryl" merely refer to replicate experiments. These results indicate that, for each of the PLGA compositions tested, at least 90% of the cumulative amount of DNA released from the PLGA/DNA-coated mesh had been released within three days of incubation. In contrast, DNA release from the polylysine-treated PLGA/DNA-coated mesh was significantly extended for each of the PLGA compositions tested, with no more than about 50% of the cumulative amount of DNA being released from the PLGA/DNA-coated mesh within twelve or thirteen days of incubation. These results demonstrate that treatment of the PLGA/DNA-coated mesh with polylysine significantly reduced the rate of release of DNA from the mesh. Thus, treatment of a polymer in which a DNA is suspended with a polycationic condensing agent significantly prolongs the period over the course of which the DNA is released from the composition at human physiological blood pH.

EXAMPLE 2

In this Example, a method for making a suture coated with a DNA-containing polymeric matrix having an exterior portion in which at least most of the DNA contained in the exterior portion of the matrix is in a condensed form. The polymeric matrix described in this Example is a lactic acid glycolic acid copolymer (PLGA), although it is understood that substantially any biocompatible polymer may be used in place of PLGA. The biocompatible polymer is preferably biodegradable (as is PLGA).

PLGA is commercially available. For example, a PLGA composition having an average molecular weight of about 90,000 and comprising about half lactate monomers and about half glycolate monomers is available from Birmingham Polymers, Inc. (Birmingham, Ala.). A suspension of PLGA in chloroform (about 3% w/v PLGA) is made by mixing PLGA and chloroform. A volume of a DNA-containing solution, such as a solution containing 1 milligram DNA, 0.5 millimolar Tris buffer, 0.5 millimolar EDTA, and having a pH of about 7.3, is combined with about 7.5 volumes of the PLGA-chloroform suspension. The resulting mixture is emulsified by vortexing the mixture for about two minutes and then sonicating the mixture for about thirty seconds at about 0° C. using a microtip probe-type sonicator set at 55 Watts output. Following this treatment, a milky emulsion is formed.

Substantially any commercially available or other suture may be coated with the milky emulsion by contacting the suture with the emulsion and the suture and permitting the emulsion to dry. Preferably, multiple layers of the emulsion are deposited on the suture by repeating this contacting and drying procedure multiple times. In one embodiment of a method of contacting the suture and the milky emulsion, a drop of the emulsion is deposited atop a hole in a support which does not absorb the emulsion. The suture is drawn through the hole, preferably in an upward direction, whereby the suture becomes coated with the emulsion. The emulsion may be dried by permitting the suture to air dry, for example, for about three minutes or longer. After one or more layers of the emulsion are deposited upon the suture, the suture is contacted with a solution which comprises a polycationic condensing agent such as polylysine, and the suture is thereafter dried. If desired, the suture may be contacted multiple times with the condensing agent-containing solution, the suture being air dried between contacting steps, to increase the proportion of the DNA molecules that are in a condensed form in the exterior portion of the matrix coating the suture.

Alternately, the suture may be contacted with the milky emulsion, dried, contacted with the condensing agent-containing solution, dried, contacted with the milky emulsion, dried, contacted with the condensing agent-containing solution, dried, and so on, for as many cycles as are desired. Using this alternate procedure, it is possible to increase the proportion of the DNA that are in a condensed form throughout the matrix coating the suture.

Preferably, the DNA which is suspended in the matrix is a nucleic acid expression vector encoding a wound healing therapeutic protein such as, for example, TGF-$\beta$, FGF, PDGF, IGF, M-CGF, BMP, GH, or PTH.

In another preferred embodiment of this suture-coating method, the DNA- and polymer-containing solution is prepared in the form of microspheres or nanospheres, for example as described in Song et al. (1997, J. Controlled Release 43:197–212). In this embodiment, the suture is still contacted with the condensing agent-containing solution, although, of course, condensing agents other than polylysine may be used, as described in the present disclosure.

EXAMPLE 3

In this Example, a method is described for preparing a matrix having a nucleic acid present substantially only on the exterior surface of the matrix and wherein at least most of the nucleic acid is present in a condensed form.

In this Example, the matrix which is used is a stainless steel intravascular stent. Stainless steel has a net positive charge in solution at pH 7.4. A polyanionic bioactive agent such as a nucleic acid may be adhered to the surface of a stainless steel object such as an intravascular stent by contacting the agent and the object. It is not necessary to add an adhesive, a coating, or any other composition to achieve association of the agent with the object. However, the amount of the polyanionic bioactive agent which may be bound to the stainless steel object is limited by the charge density and the surface area of the stainless steel object. Also, the association between the bioactive agent and the object is a relatively weak one, and the bioactive agent dissociates from the object relatively rapidly if the object is implanted into an animal.

The amount of the polyanionic bioactive agent and the duration of the period of time over which the agent is released from the stainless steel object can be increased using the following procedure.

The stainless steel object is contacted with a suspension or a solution of the polyanionic bioactive agent, resulting in binding of some of the bioactive agent to the object in a non-condensed form. The object is then optionally dried, and then contacted with a solution or suspension containing a polycationic condensing agent such as $Mg^{2+}$ or, preferably, a polycationic polymer such as polylysine. Following this treatment, the bioactive agent on the surface of the object is present in a condensed form, and an excess of the condensing agent may be present on the surface of the object, conferring a net positive charge thereto. If such an excess of condensing agent is present, then the stainless steel object having condensed bioactive agent on the surface thereof may once again be contacted with the solution containing the bioactive agent, whereby more of the bioactive agent binds to the surface of the object. The object may then be contacted again with the condensing agent-containing solution or suspension, and this cycle may be repeated as many times as desired. Optionally, the stainless steel object is dried between each contacting step.

When the stainless steel object is an intravascular stent, it is preferred that the polyanionic bioactive agent be a nucleic acid selected from the group consisting of an expression vector encoding an anti-restenotic protein, and an antirestenotic antisense oligonucleotide. Preferably, the anti-restenotic protein is selected from the group consisting of TPA, TGF-β, FGF, Rb, p21, and TK. Also preferably, the anti-restenotic antisense oligonucleotide is selected from the group consisting of a c-myb antisense oligonucleotide, a c-myc antisense oligonucleotide, and a PCNA antisense oligonucleotide. These expression vectors and antisense oligonucleotides are either known in the art or can be routinely designed by the ordinarily skilled worker.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for delivery of a nucleic acid, the composition comprising the nucleic acid and a matrix having an exterior portion, wherein at least most of the nucleic acid present at the exterior portion of the matrix is in a condensed form.

2. The composition of claim 1, wherein substantially all of the nucleic acid present at the exterior portion of the matrix is in a condensed form.

3. The composition of claim 1, wherein the exterior portion has an exterior surface and wherein the nucleic acid is present substantially only on the exterior surface of the exterior portion of the matrix.

4. The composition of claim 1, wherein the matrix comprises a plurality of the exterior portions.

5. The composition of claim 1, the matrix further comprising an interior portion having the nucleic acid suspended therein, wherein less than most of the nucleic acid in the interior portion of the matrix is not in a condensed form.

6. The composition of claim 5, wherein the matrix comprises a plurality of alternating the exterior portions and the interior portions.

7. The composition of claim 1, wherein the exterior portion comprises a polycationic condensing agent.

8. The composition of claim 7, wherein the polycationic condensing agent is selected from the group consisting of a polylysine, polyarginine, polyornithine, polyhistidine, myelin basic protein, a low molecular weight glycopeptide, a cationic amphiphilic alpha-helical oligopeptide having a repeating sequence, a galactosylated histone, $Mg^{2+}$, $Ca^{2+}$, $Co^{3+}$, $La^{3+}$, $Al^{3+}$, $Ba^{2+}$, $Cs^+$, polybrene, spermine, spermidini, prolamine, polyethylenimine, putrescine, cadaverine, and hexamine.

9. The composition of claim 8, wherein the polycationic condensing agent is poly-L-lysine.

10. The composition of claim 7, wherein the nucleic acid is selected from the group consisting of a plasmid, a linear DNA molecule, and a linear RNA molecule.

11. The composition of claim 10, wherein the nucleic acid is selected from the group consisting of an expression vector encoding a wound healing therapeutic protein, an expression vector encoding an anti-restenotic protein, and an anti-restenotic antisense oligonucleotide.

12. The composition of claim 11, wherein the nucleic acid is an expression vector encoding a wound healing therapeutic protein selected from the group consisting of TGF-β, FGF, PDGF, IGF, M-CGF, BMP, GH, and PTH.

13. The composition of claim 10, wherein the nucleic acid is an expression vector encoding an anti-restenotic protein selected from the group consisting of TPA, TGF-β, FGF, Rb, p21, and TK.

14. The composition of claim 10, wherein the nucleic acid is an anti-restenotic antisense oligonucleotide selected from the group consisting of a c-myb antisense oligonucleotide, a c-myc antisense oligonucleotide, and a PCNA antisense oligonucleotide.

15. The composition of claim 1, wherein the matrix is selected from the group consisting of a charged biocompatible material, a biocompatible polymer, a biodegradable polymer, a biocompatible biodegradable polymer.

16. The composition of claim 15, wherein the biodegradable polymer is a polylactate/polyglycolate copolymer.

17. A surface coated with the composition of claim 1.

18. An implantable device having a surface coated with the composition of claim 1.

19. The implantable device of claim 18, wherein the device is selected from the group consisting of a wound dressing, a suture, a particle, a vascular stent, and a bulk material.

20. The implantable device of claim 19, wherein the device is a vascular stent, wherein the biodegradable matrix is a polylactate/polyglycolate copolymer, wherein the nucleic acid is selected from the group consisting of an expression vector encoding an anti-restenotic protein and an anti-restenotic antisense oligonucleotide, and wherein the exterior portion further comprises polylysine.

21. The implantable device of claim 20, wherein the nucleic acid is an expression vector encoding an anti-restenotic protein selected from the group consisting of TPA, TGF-β, FGF, Rb, p21, and TK.

22. The implantable device of claim 20, wherein the nucleic acid is an anti-restenotic antisense oligonucleotide selected from the group consisting of a c-myb antisense oligonucleotide, a c-myc antisense oligonucleotide, and a PCNA antisense oligonucleotide.

23. The implantable device of claim 19, wherein the device is a suture coated with a plurality of layers of the matrix, wherein the biodegradable matrix is a polylactate/polyglycolate copolymer, wherein the nucleic acid is an expression vector encoding a wound healing therapeutic protein.

24. The implantable device of claim 23, wherein the wound healing therapeutic protein is selected from the group consisting of TGF-β, FGF, PDGF, IGF, M-CGF, BMP, GH, and PTH.

25. The implantable device of claim 23, wherein the device is coated with at least twenty layers of the matrix.

26. The implantable device of claim 19, wherein the device is a particle and wherein the nucleic acid is selected from the group consisting of an expression vector encoding a wound healing therapeutic protein, an expression vector encoding an anti-restenotic protein, and an anti-restenotic antisense oligonucleotide.

27. The implantable device of claim 26, wherein the nucleic acid is an expression vector encoding a wound healing therapeutic protein selected from the group consisting of TGF-β, FGF, PDGF, IGF, M-CGF, BMP, GH, and PTH.

28. The implantable device of claim 26, wherein the nucleic acid is an expression vector encoding an anti-restenotic protein selected from the group consisting of TPA, TGF-β, FGF, Rb, p21, and TK.

29. The implantable device of claim 26, wherein the nucleic acid is an anti-restenotic antisense oligonucleotide selected from the group consisting of a c-myb antisense oligonucleotide, a c-myc antisense oligonucleotide, and a PCNA antisense oligonucleotide.

30. The implantable device of claim 26, wherein the particle has a diameter no greater than about 900 micrometers.

31. The implantable device of claim 30, wherein the particle has a diameter no greater than about 1 micrometer.

32. The implantable device of claim 19, wherein the device is a bulk material and wherein the nucleic acid is selected from the group consisting of an expression vector encoding an oncogene and an antisense oligonucleotide directed against an oncogene.

33. The implantable device of claim 32, wherein the nucleic acid is an expression vector encoding an oncogene selected from the group consisting of abl, akt2, apc, bcl2α, bcl2β, bcl3, bcr, brcal, brca2, cbl, ccnd1, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf1, wnt1, wnt2, wt1, and yes1.

34. A surface coated with the composition of claim 5, wherein the interior portion is interposed between the surface and the exterior portion.

35. An implantable device having a surface coated with the composition of claim 5, wherein the interior portion is interposed between the surface and the exterior portion.

36. A method of making a composition for delivery of a nucleic acid, the method comprising providing a biodegradable matrix having an interior portion and an exterior portion, wherein the nucleic acid is suspended in the biodegradable matrix in a non-condensed form; and contacting the exterior portion of the biodegradable matrix with a polycationic condensing agent, whereby at least most of the nucleic acid assumes a condensed form at the exterior portion of the biodegradable matrix.

37. A method of making a composition for delivery of a nucleic acid, the method comprising providing a matrix which has an exterior portion and which comprises the nucleic acid at the exterior portion; and contacting the exterior portion of the matrix with a polycationic condensing agent, whereby at least most of the nucleic acid assumes a condensed form at the exterior portion of the matrix.

38. A method of delivering a nucleic acid to an animal tissue, the method comprising placing in fluid communication with the animal tissue a composition comprising the nucleic acid and a matrix having an exterior portion, wherein at least most of the nucleic acid is in a condensed form at the exterior portion of the matrix.

39. A kit comprising a biocompatible matrix having an exterior portion and an instructional material which describes combining the matrix with a nucleic acid and condensing at least most of the nucleic acid at the exterior portion of the matrix.

40. A kit comprising a composition comprising a nucleic acid and a biocompatible matrix having an exterior portion, wherein at least most of the nucleic acid present at the exterior portion of the matrix is in a condensed form, and an instructional material which describes administration of the composition to a tissue of an animal to effect delivery of the nucleic acid to the tissue.

41. A kit for coating an implantable device with a composition for delivery of a nucleic acid upon implantation of the device, the kit comprising a nucleic acid, a biocompatible polymeric matrix suspended in a solvent and a polycationic condensing agent, whereby at least most of the nucleic acid assumes a condensed form.

42. A kit for coating an implantable device with a composition for delivery of a nucleic acid upon implantation of the device, the kit comprising a nucleic acid, a suspension of monomers of a biocompatible polymeric matrix, a polymerization initiator, and a polycationic condensing agent, whereby at least most of the nucleic acid assumes a condensed form.

43. A method of storing a nucleic acid, the method comprising suspending the nucleic acid in a matrix and contacting the matrix with a polycationic condensing agent, whereby at least most of the nucleic acid in the matrix assumes a condensed form.

44. The composition of claim 1, wherein the matrix is selected from the group consisting of polylactic acid, polyglycolic acid, polycaprolactone, a copolymer of polylactic acid and polyglycolic acid, a copolymer of polylactic acid and polycaprolactone, a copolymer of polyglycolic acid and polycaprolactone, a polygylcolide, a polyanhydride, a polyacrylate, a polyalkyl cyanoacrylate, n-butyl cyanoacrylate, isopropyl cyanoacrylate, a polyacrylamide, a polyorthoester, a polyphosphazene, a polypeptide, a polyurethane, a polystyrene, a polystyrene sulfonic acid, a polystyrene carboxylic acid, a polyalkylene oxide, a polyethylene, a polyvinyl chloride, a polyamide, a nylon, a polyester, a rayon, a polypropylene, a polyacrylonitrile, an acrylic, a polyisoprene, a polybutadiene, a polybutadiene-polyisoprene copolymer, a neoprene, a nitrile rubber, a polyisobutylene, an olefinic rubber, an ethylene-propylene rubber, an ethylene-propylene-diene monomer rubber, a polyurethane elastomer, a silicone rubber, a fluoroelastomer, a fluorosilicone rubber, a vinyl acetate homopolymer, a vinyl acetate copolymer, an ethylene vinyl acetate copolymer, an acrylates homopolymer, an acrylates copolymer, polymethylmethacrylate, polyethylmethacrylate, polymethacrylate, ethylene glycol dimethacrylate, ethylene dimethacrylate, hydroxymethyl methacrylate, a polyvinylpyrrolidone, a polyacrylonitrile butadiene, a polycarbonate, a polyamide, a fluoropolymer, polytetrafluoroethylene, polyvinyl fluoride, a polystyrene, a styrene acrylonitrile homopolymers, a styrene acrylonitrile copolymer, a cellulose acetate, an acrylonitrile butadiene styrene homopolymer, a acrylonitrile butadiene styrene copolymer, a polymethylpentene, a polysulfone, a polyester, a polyimide, a polyisobutylene, a polymethylstyrene, an alginate, an agarose, a dextrin, a dextran, a multiblock polymer, a biocompatible metal alloy, titanium, platinum, stainless steel, hydroxyapatite, tricalcium phosphate, and cocoa butter.

* * * * *